(12) United States Patent
Ganey

(10) Patent No.: US 11,738,118 B2
(45) Date of Patent: *Aug. 29, 2023

(54) INFUSED CARTILAGE PARTICLES

(71) Applicant: Vivex Biologies Group, Inc., Atlanta, GA (US)

(72) Inventor: Timothy Ganey, Tampa, FL (US)

(73) Assignee: Vivex Biologies Group, Inc., Atlanta, GA (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/018,523

(22) Filed: Sep. 11, 2020

(65) Prior Publication Data
US 2022/0080082 A1 Mar. 17, 2022

(51) Int. Cl.
*A61L 27/38* (2006.01)
*A61L 27/36* (2006.01)

(52) U.S. Cl.
CPC ....... *A61L 27/3886* (2013.01); *A61L 27/3608* (2013.01); *A61L 27/3687* (2013.01); *A61L 27/3691* (2013.01); *A61L 27/3852* (2013.01); *A61L 2300/802* (2013.01)

(58) Field of Classification Search
CPC ............ A61L 27/3608; A61L 27/3691; A61L 27/3852; A61L 2300/802; A61L 2430/06; A61L 27/3654

See application file for complete search history.

(56) References Cited

U.S. PATENT DOCUMENTS 6,511,958 B1 * 1/2003 Atkinson ................ A61L 27/26
514/13.8
2018/0325830 A1 * 11/2018 Ganey ................ A61L 27/3608

* cited by examiner

*Primary Examiner* — Andrew S Rosenthal
(74) *Attorney, Agent, or Firm* — David L. King

(57) ABSTRACT

A method of making infused non-demineralized cartilage particles employs the following steps: cutting or shaving cartilage tissue into cartilage particles, washing the particles, and infusing the particles with a supernatant of biologic material or a polyampholyte cryoprotectant or a combination of both to create infused particles.

48 Claims, 17 Drawing Sheets

12   25

Cartilage   Conditioned Cell Supernatant   Polyampholyte CryoProtectant 10   25, 30

Figure 2 Particle size (A) and zeta potential (B) of PIC at different C/A ratios (n=3).
Abbreviations: C/A ratio, ratio of cationic PEI and anionic P(Asp) block; P(Asp), poly(aspartic acid); PIC, polyelectrolyte ionomer complex.

INFUSED CARTILAGE PARTICLES

TECHNICAL FIELD

This invention is a microfracture or cartilage defect grafting composition and method of manufacturing made from cartilage particles or cartilage particle mixtures infused with an acellular biologic material and/or a cryoprotectant.

BACKGROUND OF THE INVENTION

Cartilage, particularly articular cartilage, of higher animals, including man, has a limited potential for repair. Following injuries to articular cartilage, the cartilage generally does not repair itself because of its limited capacity for regeneration. The ability to repair is dependent on the extent and the depth of injury and the surviving chondrocytes and normal articular cartilage matrix. In injuries involving subchondral bone, there is no regeneration of the cartilage, but there is typically enlargement and progression of the lesion with associated pain.

The ultimate goal of treatment of these lesions is restoration of the cartilage underlying subchondral, and the integration of both tissues; in most cases, this is not achieved.

Adult articular cartilage is not vascularized and, as stated above, lacks the capacity to regenerate itself after sustaining damage (Vangness, C. T., Jr. et al., Am. J. Orth. 33, No. 25S: 29, 2004). When cartilage is cut, without involvement of subchondral bone, the defect often will persist for the duration of the individual's life.

Treatment of articular cartilage defects may be either surgical or non-surgical. For example, several operative procedures are currently used to repair or remove damaged cartilage in order to prevent further destruction of the joint, decrease pain, and restore function. These include arthroscopic debridement and lavage, subchondral bone stimulating procedures, transplantation of chondrocytes or cartilage autografts and allografts and total knee arthroplasty. However, none of these techniques have demonstrated success in regenerating the native articular cartilage.

Thus, there is a desire for materials and methods for stimulating chondrogenesis.

The present invention achieves this objective using cartilage particles that are infused with an acellular biologic material and/or a cryoprotectant to enhance new growth. These and other objectives are explained hereinafter.

SUMMARY OF THE INVENTION

A method of making infused non-demineralized cartilage particles employs the following steps: cutting or shaving cartilage tissue into cartilage particles, washing the particles, and infusing the particles with a supernatant of biologic material or a polyampholyte cryoprotectant or a combination of both to create infused particles.

The step of infusing includes exposing the cartilage particles to a negative pressure or vacuum to draw the supernatant and/or the polyampholyte cryoprotectant into the particles, or alternatively, exposing the cartilage particles to a positive pressure to drive the supernatant and/or the polyampholyte cryoprotectant into the particles. The particles can have a maximum greatest diameter of 100 µm to 300 µm. The method may include freezing the supernatant and/or the polyampholyte cryoprotectant infused cartilage particles in volume greater that the total volume of the cartilage particles; variation ranging from 1% to 200% of the material. In one embodiment, the cartilage particles are suspended in cryoprotectant allowing some seepage of the evaporate that can be increased by exposure to acoustic shock wave pressure pulses which draw down the liquid while allowing all the evaporate to be driven or left within or lying on the infused particles.

The step of cutting or shaving includes passing the cartilage through a cutting die to form shaped particles, wherein the shaped particles have a trapezoidal or triangular cross-section. The method may further include the step of drying the infused particles, wherein the step of drying includes freeze-drying by lyophilization. The method further may include one or more of the steps of shaping, extrusion, molding or flattening the dried particles into sheets to form random particle stacked matting. Alternatively, a cryomilling technique for pulverizing as the method of variable sizing could be used.

The resultant method creates an infused cartilage grafting composition having cartilage particles infused with one or more of a supernatant of biologic material or a polyampholyte cryoprotectant or both wherein the supernatant is derived from one or more of a fatty and a cellular marrow. The supernatant includes a mixture of biologic material having non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function. A volume of a polyampholyte cryoprotectant can be used to infuse the particles alone or can be intermixed with the supernatant including the mixture of biologic material, wherein the polyampholyte cryoprotectant forms a three-dimensional infusion impregnating and coating externally enveloping each of the particles along with each of the non-whole cellular components, if any, and each of the whole cells, if any, of the mixture of biologic material. The polyampholyte cryoprotectant can be a liquid of a polyamine polymer compound of carboxylated poly-lysine. The infusion of the fibers buffers inflammation, sustains regenerative potential and biologic function of the mixture during preservation and implantation.

The infused composition with the infusion coating is configured to be metabolized after implantation after a predetermined time of three or more days up to six days.

In one embodiment, the infused composition has the infused particles randomly compressed into a matting or sheet. A plurality of the matting or sheets can be stacked to form a laminated stack, wherein each sheet or mat can have a distinct C (cation)/A (anion) ratio between nitrogen atom of the cationic polymer and carboxyl group of an anionic and stacking the sheets or mats together is configured to create a range variation of C/A ratios across the layers of the laminate to control nano-dimensions accentuating zeta potential for enhancing exosome absorption by creating a gradient of molecular potential when implanted.

The polyampholyte cryoprotectant forms a strong hydrophilic characteristic of the infusion coating to protect the non-whole cellular components if any and the contents of the whole cells if any. The mixture of biologic material is mechanically selected biologic material derived from fatty tissues, placental tissue or bone marrow. The mixture of mechanically selected biologic material derived from aforementioned sources of tissue further includes a select number of non-whole cell fractions including one or more of exosomes, transcriptosomes, proteasomes, membrane rafts, lipid rafts. The biological mixture is predisposed to demonstrate or support elaboration of active volume or spatial geometry consistent in morphology with that of endogenous cartilage. The biological mixture extends regenerative resonance that compliments or mimics cartilage tissue complexity. The mixture is treated in the cryoprotectant prior to preservation or cryopreservation or freeze drying.

The cryoprotectant creates a physical, electrical, chemical gradient, or combination thereof for tissue regeneration, and wherein the gradient has a physical characteristic of modulus or topography such as charge density, field shape or cyto-taxic, cryo- or chemo-taxic tendencies and/or wherein the gradient has a chemical characteristic of spatially changing compositions of density or species of functional molecules, wherein the molecules can offer a fixed catalytic function as a co-factor and/or wherein the gradient has an electrical characteristic of charge based or pH based or electron affinities that confer metastability in biologic potential.

The mixture which is derived from a cadaver has separation-enhanced non-whole cell fractions vitality including one or more of the following: separating the fractions from cells heightens their vitality, reversing "arrest" of donors, accentuating responsive molecular coupling, matrix guarding in neutralizing inflammation or providing a basis for metabolic satience by balancing stimulus for repair. Determinate separation is possible by various isolation modalties; i.e. ultracentrifugation, polymer precipitation, immunoisolation.

The infused composition in one embodiment has the cryoprotectant being a cryoprotectant polyampholyte of carboxylated polylysine and wherein the percentages of carboxylation can be altered to control exosome size, matrix voltages and/or zeta potential wherein the carboxylic percentage adjustment varies, a C/A ratio, a ratio between a nitrogen atom of a cationic polymer and a carboxyl group representing a anionic, wherein the zeta potential for enhancing exosome absorption is achieved by creating a gradient of molecular potential by adjusting the carboxyl ratio of the protectant. The regenerative resonance occurs in the presence or absence of a refractory response. The cryopreservation occurs at a temperature that is sub-freezing. The cryopreservation temperature is from 0 degrees C. to −200 degrees C. The mixture creates a physical or electrical or chemical gradient or combination thereof for tissue regeneration. The gradient can be a physical characteristic such as modulus or topography. The gradient can be a chemical characteristic such as spatially changing compositions of density or species of functional molecules. The gradient can be an electrical characteristic such as charge based or pH based. The biological mixture contains organelle fragments. The infused cartilage grafting composition may have the electrical characteristic such as a positive zeta potential formed in the infused composition to ensure uptake of nano-particles into cells when implanted as a result of a positive surface charge causing an electrostatic interaction between negatively charged cellular membranes and the positively charged infused fibers. The infused composition can be maintained at ambient temperature prior to freeze drying.

The infused composition in one embodiment has the particles infused with a polyampholyte cryoprotectant for direct implantation wherein said protectant is a 1-50 w/w % aqueous solution of at least one polyamine polymer compound comprised of at least one polymer of units having side-chain amino groups, said at least one polymer of units being selected from a group consisting of ε-poly-L-lysine, α-poly-L-lysine, poly-arginine, allylamine polymer and partially methoxy-carbonylated allylamine polymer; and 50-99 mol % of amino groups, other than those forming amino-acid-to-amino-acid linkages, of said at least one polymer compound is blocked with carboxylic anhydride to form pendant moieties, each of which is linked to main chain of the polymer via an amide linkage and essentially has a not-blocked carboxylic group. Said protectant liquid is obtained by dissolving the at least one polyamine polymer compound in a physiological solution, wherein the physiological solution is a saline, Dulbecco-modified eagle MEM culture medium (DMEM), or a culture medium for cells or tissues. Said at least one polymer compound is ε-poly-L-lysine having number-average molecular weight in a range of 1000-20,000 and wherein remaining side-chain amino groups or remaining side-chain and terminal amino groups of the at least one polymer compound are not blocked by covalent bonding.

DEFINITIONS

Abbreviations: C/A ratio, ratio of cationic PEI and anionic P (Asp) block; P (Asp), poly(aspartic acid); PIC, polyelectrolyte ionomer complex.

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

Dimethyl sulfoxide (DMSO) is an organosulfur compound with the formula $(CH_3)_2SO$. This colorless liquid is an important polar aprotic solvent that dissolves both polar and nonpolar compounds and is miscible in a wide range of organic solvents as well as water. It has a relatively high melting point and is not suitable for direct implantation and requires cell washing due to its toxic characteristics.

DPBS—Dulbecco's Phosphate Buffered Saline.

CBT-MIXER—Mixing blade for Cancellous Bone Tumbler Jar.

Chimera—A genetic chimerism or chimera (also spelled chimaera) is a single organism composed of cells with distinct genotypes.

Cold Media—Media used during the preparation of vertebral bodies for initial processing.

Cryopreserved—Tissue frozen with the addition of, or in a solution containing, a cryoprotectant agent such as glycerol, or dimethylsulfoxide, or carboxylated poly-1-lysine.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed vertebral bodies prior to bone decellularization.

PBS—Phosphate Buffered Saline.

Processing Media—Media used during bone decellularization that may contain DMEM/Low Glucose no phenol red, Human Serum Albumin, Heparin, Gentamicin and DNAse.

BRIEF DESCRIPTION OF THE DRAWINGS

The invention will be described by way of example and with reference to the accompanying drawings in which:

FIG. 17 shows a range from C/A 0.125 to C/A of 8 yielding a 64 times delta or difference potential.

DETAILED DESCRIPTION OF THE INVENTION

Figure 1:
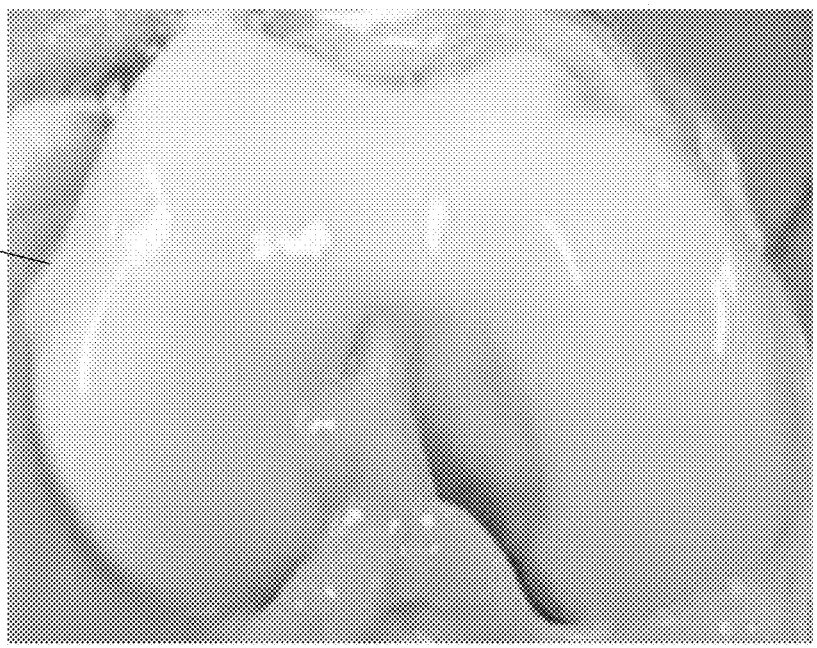
FIG. 1 is a representation of cartilage taken from a cadaver.

The failure of current microfracture techniques or cartilage defect scaffolds or fillers as compositions divested of morphology address the shortcomings of inadequate biological impetus to repair if not fully regenerate articular cartilage. This application and invention proposes high pressure substitution of supernatant material from bone marrow that is enriched with exosomes, and micro-ma (miRNA) materials. In practice, the manufacturing process is designed to accommodate a drying step which is known in the art, but to seek a divergent interest in next steps where the material is perfused under high pressure with the supernatant rich material from bone marrow processing. This material is replete with exosomes and has bioactive properties. A second step, or a combination of steps is next offered as novel technology. By using variation in substitution of cryoprotectant, the application notes other fields of polymer research that have varied amide and carboxyl linkage to better control nano-particle size, and mV electropotential in delivery devices for cancer therapy. In this specific application, the ability to use the variations in voltage to not only control size but create standing voltage differences is novel is aligned to accepted stratregies utilizing zeta-potential to guide metabolic activities and elaborate cell cell differentiation lineages Along with the HCTP controlled use of the basis of cryoprotectants, the value is novel nano-sizing, cell merging value, and provide infused cartilage particles with exosome value. Alternatively, the use of low pressure vacuum differentials can be used to impregnate and infuse the particles with the supernatant and/or cryoprotectant.

These and other benefits of the present invention and the method of preparing it are described hereinafter.

Dr. Kazuaki Matsumura has developed a Cryoprotectant that substitutes carboxylation for amide groups to balance the charge. The present invention expands these features in unique ways.

Current technology is driving to smart nanomedicine that incorporates the ability to use mV variations to enhance or reduce the potency of drug delivery. A positive zeta potential of the complexes ensures the uptake of nanoparticles into cells, since a positive surface charge allows an electrostatic interaction between the negatively charged cellular membranes and the positively charged complexes.

C/A Ratio and Carboxyl Substitution, Various C/A ratios (ratio between the nitrogen atom of the cationic polymer and the carboxyl group representing the anionic)

The original Matsumura patent for carboxylated polylysine provides the range of 50-99% blockage of amide moieties and as such the potential for variations in the C/A ratio is appropriate to improvements in C/A ratio control.

The goal is to protect the potential for specifying and controlling nano-dimension, accentuating zeta potential for enhancing exosome absorption, and utilizing adjustment in the cryoprotectant for fractioning and creating gradients of molecular potential. Multi-Laminate made from sheets or mats of the infused bone particle composition allows for nano-electrical dimension control, control of mV charge and variation between particle entities, Zeta-potential variability, exosome sizing control, and pH response variability during wound healing.

Exosome size and matrix voltage and zeta potential can be controlled with carboxylation of the cryoprotectant. Exosome interaction is essential to the attachment of cells to matrix. Work in Migrasomes has shown additional specificity for exosome and matrix molecular entity, accenting affinity for integrins, and coalescing exosomes as surface ligands for exchange during cell migration.

The present invention has a clear path for exosomes derived from one or more of adipose tissue, placental tissue or bone marrow, cryoprotectant in range that can be used to create unique mats, and a biomedical manufacturing facility to develop novel products. Short term value in matted, molded, or extruded materials, but long-term novelty in controlling electrophysical nature of advanced materials is explained herein.

In accordance with the present invention, particulate cartilage compositions for stimulating chondrogenesis and producing cartilage regeneration comprise non-demineralized particulate articular cartilage. Articular cartilage may be obtained from the articular surfaces of joints, such as from distal femurs, proximal tibias, acetabulums, heads of femurs, and/or heads of radiuses. The cartilage may be removed, for example, with a scalpel blade and is preferably removed down to subchondral bone, without removing bone. The articular cartilage for use in the present invention may include articular hyaline cartilage and/or fibrocartilage and may comprise allogeneic and/or xenogeneic cartilage.

The articular cartilage is preferably non-demineralized. Preferably, the cartilage is not subjected to harsh chemical treatments, which can alter the inherent natural properties of material within the cartilage. For example, the cartilage is preferably not subjected to demineralization treatments such as treatment with hydrochloric acid, ethylene diamine, and/or other demineralization agents. In some embodiments, the non-demineralized articular cartilage may be subjected to microbiological testing or subjected to other testing protocols that do not deleteriously alter the cartilage, but reduce risk of bioburden Additionally, the articular cartilage is not subjected to any physical treatments that may demineralize and/or alter the inherent natural properties of the cartilage. For example, the articular cartilage is preferably not subjected to elevated temperatures, e.g., temperatures greater than about $50°$ C., that may diminish the chondrogenic activity of the cartilage. However, the articular cartilage may be preserved, e.g., freeze-dried, frozen, and/or dried, after being removed from the joint. One preferred method of preserving articular cartilage is freeze-drying.

The composition includes non-demineralized cartilage particles preferably having a distribution of particle sizes. The articular cartilage particles may have sizes distributed within the range of from about 60 microns to about 500 microns, more preferably distributed in the range of from about 60 microns to about 250 microns. Some compositions, according to the present invention, may include cartilage particles having particle sizes of less than about 250 microns, i.e., cartilage powder. Some compositions may include cartilage particles having a distribution of particle sizes in the range of from about 250 microns to about 500 microns, i.e., cartilage granules. In some embodiments, the composition may comprise a combination of cartilage powder and cartilage granules.

Cartilage compositions according to the present invention may be produced by grinding non-demineralized articular cartilage to produce particles having the preferred distribution of particle sizes. The cartilage may be sourced in the form of dry cartilage, freeze-dried cartilage, frozen cartilage, wet cartilage or mixtures thereof. In one preferred embodiment, the cartilage is freeze-dried. For example, pieces of cartilage obtained from the articular surface of one or more joints are washed in several changes of normal saline, blotted dry, and frozen rapidly, e.g., at $10°$ C./min or faster, in the vapor phase of liquid nitrogen (about $-150°$ C.) or alternatively in the liquid phase of liquid nitrogen (about $-196°$ C.). After being frozen, the cartilage is preferably rapidly placed directly on the shelves of a freeze-drying apparatus maintained at about $-40°$ C. to about $-50°$ C. (the condenser being cooled to from about $-70°$ C. to about $-80°$ C.). A vacuum level of less than about 100 millitorr is preferably maintained in the freeze-drying chamber during the freeze-drying cycle. The freeze-drying cycle may last an average of about 5 days. During the initial 30-45 minutes of the cycle, the cartilage warms from the initial frozen temperature (e.g., about $-150°$ C.) to the temperature of the freeze-drying chamber (e.g., about $-40°$ C.), after which it is maintained at about $-40°$ C. for the remainder of the cycle. Preferably, the moisture content of the cartilage is reduced from about 4 to about 5%. Overdrying is preferably avoided, as this may result in the irreversible alterations of collagen and proteoglycan structures. At the end of the freeze-drying cycle, the chamber is warmed to room temperature, the vacuum released and the freeze-dried cartilage is removed.

The non-demineralized articular cartilage may be ground using any suitable grinding apparatus. For example, any grinding apparatus capable of grinding dry, hard, brittle material in seconds, such as turbo mills, disc mills, toothed disc mills, jet mills or other similar apparatuses are suitable.

Figure 31:
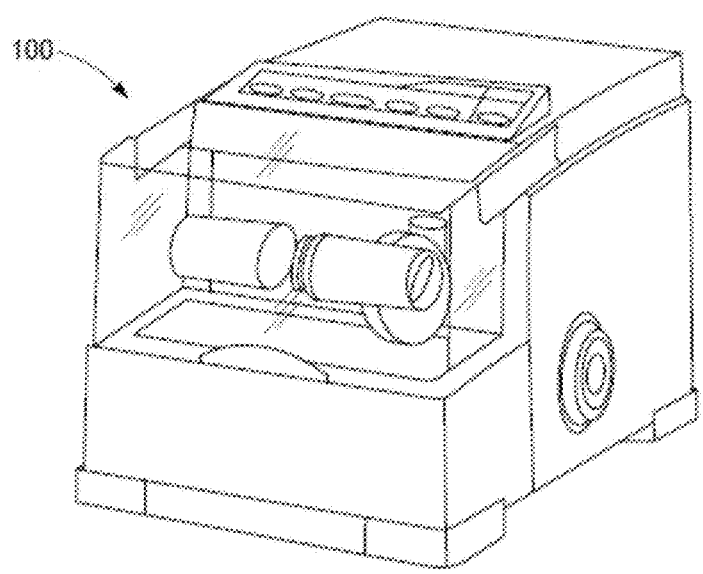
FIG. 31 is a photo of an exemplary cryomill.

Preferably, grinding is performed under conditions that preclude raising the temperature of the non-demineralized articular cartilage to a level that may diminish the chondrogenic activity of the composition. For example, grinding is preferably performed without raising the temperature of the articular cartilage above about $50°$ C. In some embodiments, grinding is preferably performed without raising the temperature of the cartilage above about $40°$ C. The temperature of the articular cartilage may be measured in any suitable manner. For example, thermocouples may be used to monitor the temperature of the cartilage directly, e.g., by measuring the temperature of the cartilage immediately after grinding, or indirectly, e.g., by measuring the temperature of the metal in the grinding mill. Continuous grinding in conventional grinding mills for 3-5 minutes can raise the temperature of the material to $70°$ C. or above. However, operating a grinding mill intermittently may preclude an undesirable rise in temperature. In one embodiment, freeze-dried pieces of cartilage, 1-4 mm in size, may be ground in a grinding mill operating intermittently for 20-30 second intervals. An exemplary cryomill is shown in FIG. 31.

After each grinding cycle, the cartilage may be sieved. The cartilage may be sieved through sieves of 100 to 500 microns. Sieving may be used to separate cartilage into cartilage powder (i.e., particle sizes of less than 250 microns) and cartilage granules (i.e., particle sizes of 250 to 500 microns). Grinding may be repeated until the desired distribution of particles sizes is obtained.

A separate embodiment departs from other earlier manufacturing techniques and supports cartilage compositions as a present invention advancing articular cartilage techniques to produce particles with additional protection of polyampholyte cryoprotectant to retain factors inherent to matrix, cell, secretions, and factors that contribute to tissue homeostasis and repair. While cartilage in this embodiment is similarly sourced in the form of dry cartilage, freeze-dried cartilage, frozen cartilage, wet cartilage or mixtures thereof, an inaugural event of this preferred embodiment includes the additional of a cryoprotectant immediately after the initial wash phases before the cartilage is freeze-dried. For example, pieces of cartilage obtained from the articular surface of one or more joints are washed in several changes of normal saline, blotted dry, and then suspended in a polyampholyte. A vacuum level of less than about 100 millitorr is preferably maintained in the freeze-drying chamber to fully infiltrate the cartilage matrix, reach an equilibrium of free water and polyampholyte at 37 degrees for up to 24 hours. In some embodiments, this range comprises a physiologic range comprising between approximately 35-41 degrees Centigrade, inclusive, to take advantage of pyrogenic cytokines and their effective activity on cell shedding and reaction during the preparation and water extraction phases.

Tissue is completely immersed in the cryoprotectant during the incubation phase. During the freeze-drying cycle. Cryoprotectant and cartilage particles are frozen rapidly, e.g., at 10° C./min or faster, in the vapor phase of liquid nitrogen (about −150° C.) or alternatively in the liquid phase of liquid nitrogen (about −196° C.). After being frozen, the embedded and protected cartilage particles cryoprotectant are placed directly on the shelves of a freeze-drying apparatus maintained at about −40° C. to about −50° C. (the condenser being cooled to from about −70° C. to about −80° C.). The freeze-drying cycle may last an average of about 5 days. During the initial 30-45 minutes of the cycle, the cartilage warms from the initial frozen temperature (e.g., about −150° C.) to the temperature of the freeze-drying chamber (e.g., about −40° C.), after which it is maintained at about −40° C. for the remainder of the cycle. Preferably, the moisture content of the cartilage is reduced from to about 5% and sublimated distillation removes the cryoprotectant from within the matrix particles and on the outside. The technique is further designed to take advantage of the drying process and to phase siphon the cryoprotectant into the tissue as the water content evaporates. Over drying is preferably avoided, as this may result in the irreversible alterations of collagen and proteoglycan structures. At the end of the freeze-drying cycle, the chamber is warmed to room temperature, the vacuum released, and the freeze-dried cartilage is removed. Sieving and sizing are noted previously and follow the manufacturing step designed to assure a full complement of matrix factors are not lost or altered during the preparation.

The present invention also provides a method for regenerating articular cartilage. Therapeutically effective amounts of cartilage composition comprising non-demineralized articular cartilage having particle sizes distributed within the range of from about 60 microns to about 500 microns may be administered at the site of a cartilage defect. The cartilage composition may be implanted at the articular surface and packed into the defect. Advantageously in some embodiments, the cartilage composition may be packed into the defect with the use of an overlying cover.

Without wishing to be bound to any theory, it is believed that compositions, according to the invention, including non-demineralized particulate cartilage, release cartilage growth factor(s), miRNA, exosomes, microvesicles or other substances that appropriate normal tissue metabolism, or induce regeneration of articular cartilage. The three-dimensional shape of the particles and multiple surfaces, as well as the inventive particle sizes and distributions, enhance diffusion of the cartilage growth factor(s) or other substances from the particles. Furthermore, the absence of harsh chemical treatments and avoidance of elevated temperatures during processing facilitates the production of particles having high chondrogenic activity.

The invention includes the following aspects.

1. An aspect of the invention is an infused particulate cartilage composition for stimulating chondrogenesis and producing cartilage regeneration comprising non-demineralized particulate articular cartilage having a distribution of particle sizes within the range of from about 60 microns to about 500 microns.

2. In aspect 1 of the invention, the non-demineralized particulate articular cartilage has a distribution of particle sizes within the range of from about 60 microns to about 250 microns.

3. In aspect 1 of the invention, the non-demineralized particulate articular cartilage comprises chemically untreated non-demineralized particulate articular cartilage.

4. In aspect 1 of the invention, the non-demineralized particulate articular cartilage comprises one of hyaline cartilage, fibrocartilage, and mixtures thereof.

5. In aspect 1 of the invention, the non-demineralized articular cartilage comprises one of allogeneic cartilage, xenogeneic cartilage, and mixtures thereof.

6. Another aspect of the invention includes a process for preparing a particulate cartilage composition for stimulating chondrogenesis and producing cartilage regeneration comprising grinding non-demineralized articular cartilage to particle sizes distributed within the range of from about 60 microns to about 500 microns, wherein, during grinding, the temperature of the non-demineralized articular cartilage does not exceed about 50° C.

7. In aspect 6 of the invention, during grinding, the temperature of the non-demineralized articular cartilage does not exceed about 40° C.

8. In aspect 6 of the invention, the non-demineralized articular cartilage is not chemically treated.

9. In aspect 6 of the invention, the process comprises grinding one of dry non-demineralized articular cartilage, freeze-dried non-demineralized articular cartilage, frozen non-demineralized articular cartilage, wet non-demineralized articular cartilage, and mixtures thereof.

10. In aspect 6 of the invention, the process comprises grinding one of non-demineralized allogeneic cartilage, non-demineralized xenogeneic cartilage, and mixtures thereof.

11. Another aspect of the invention includes a method for regenerating articular cartilage comprising administering infused non-demineralized particulate articular cartilage having a distribution of particle sizes within the range of about 60 microns to about 500 microns.

12. In aspect 11 of the invention, the method comprises administering one or more additional cartilage protection factors, which enhance and promote exchange of subcellular factors for directed delivery to the articular cartilage defect.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Of course, variations of those preferred embodiments will become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the-above-described elements in all possible variations thereof is encompassed by the invention unless otherwise indicated herein or otherwise clearly contradicted by context.

Figure 2:
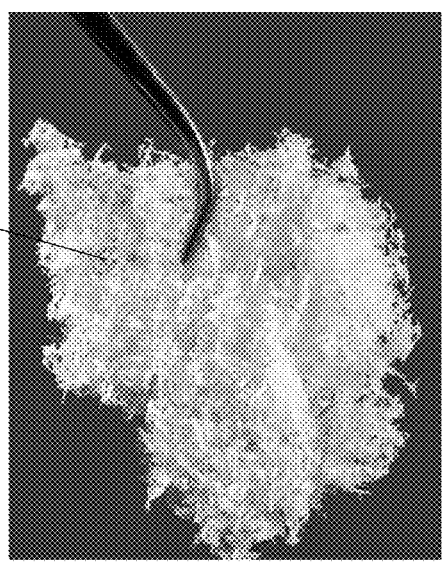
FIG. 2 is a photograph of exemplary cartilage fibers.
Figure 3:
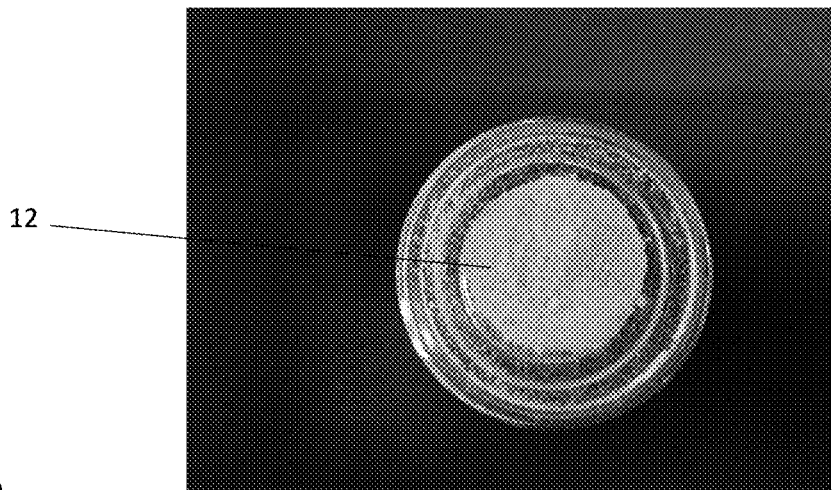
FIG. 3 is a photograph of exemplary cartilage particles.

With reference to FIG. 1, an exemplary cartilage 2 from a cadaver is shown. FIG. 2 is a photograph showing exemplary cartilage fibers 12F. FIG. 3 is a photograph showing exemplary cartilage particles 12.

Figure 4:
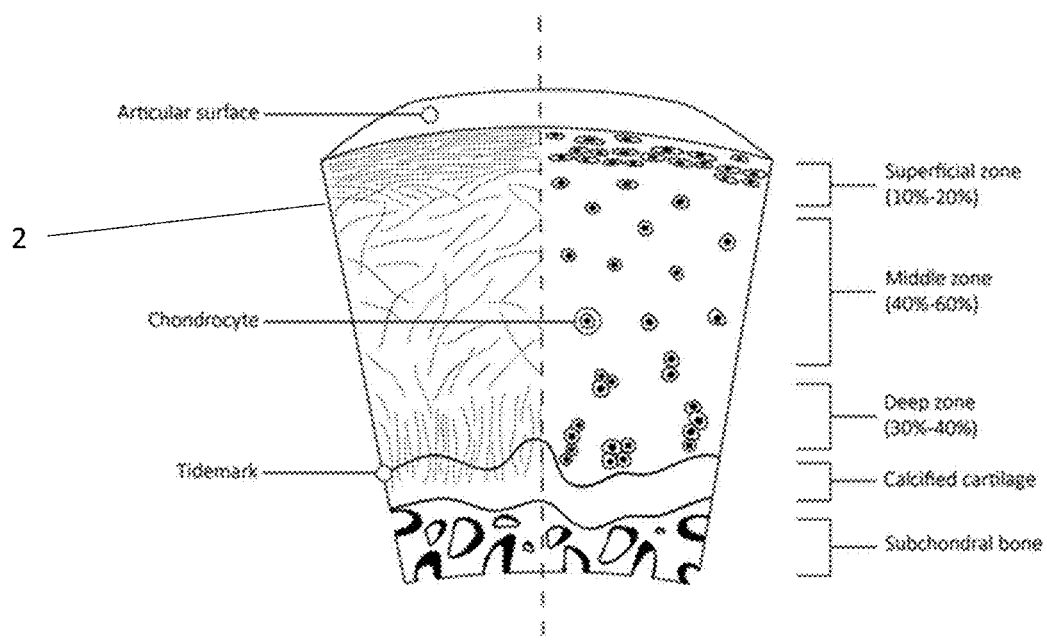
FIG. 4 is a schematic illustration of a cartilage tissue.
Figure 5:
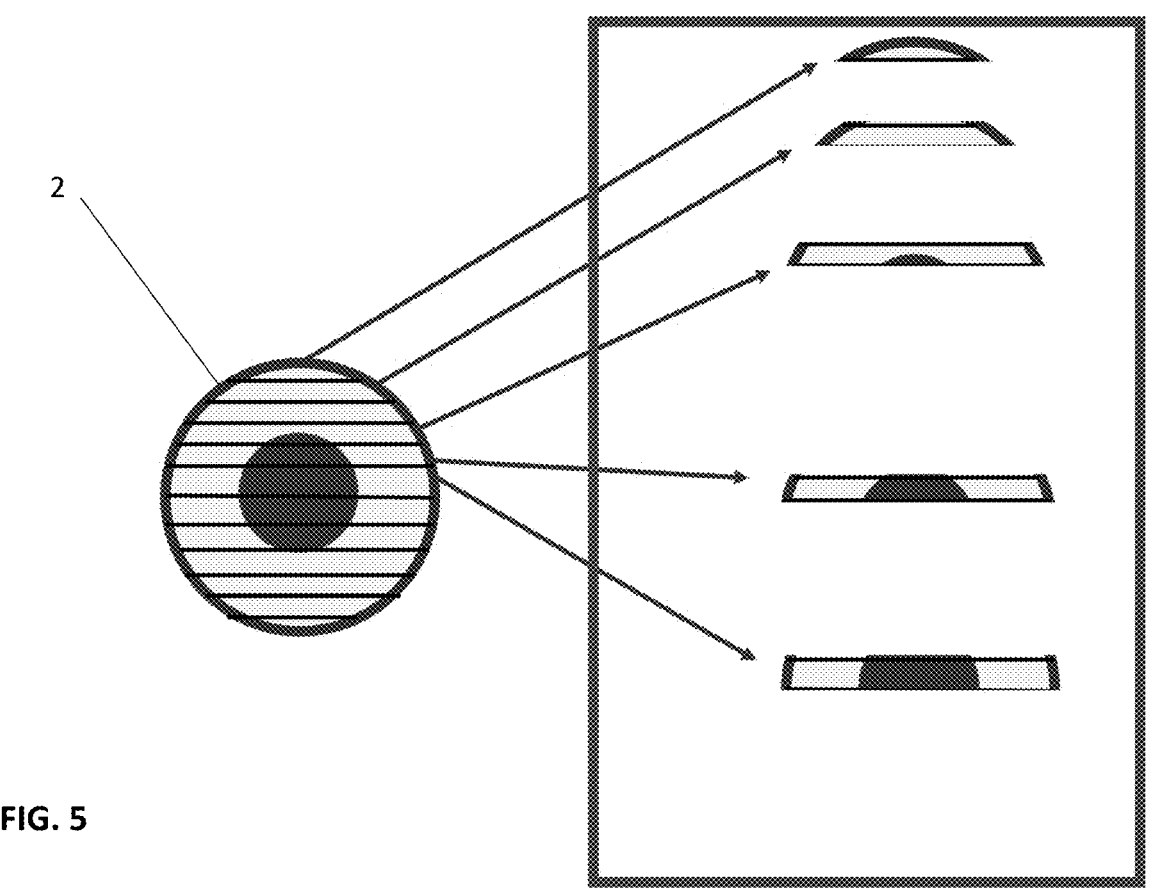
FIG. 5 is a schematic end view of FIG. 4 showing the cartilage tissue shaved into thin sections and collected.
Figure 6:
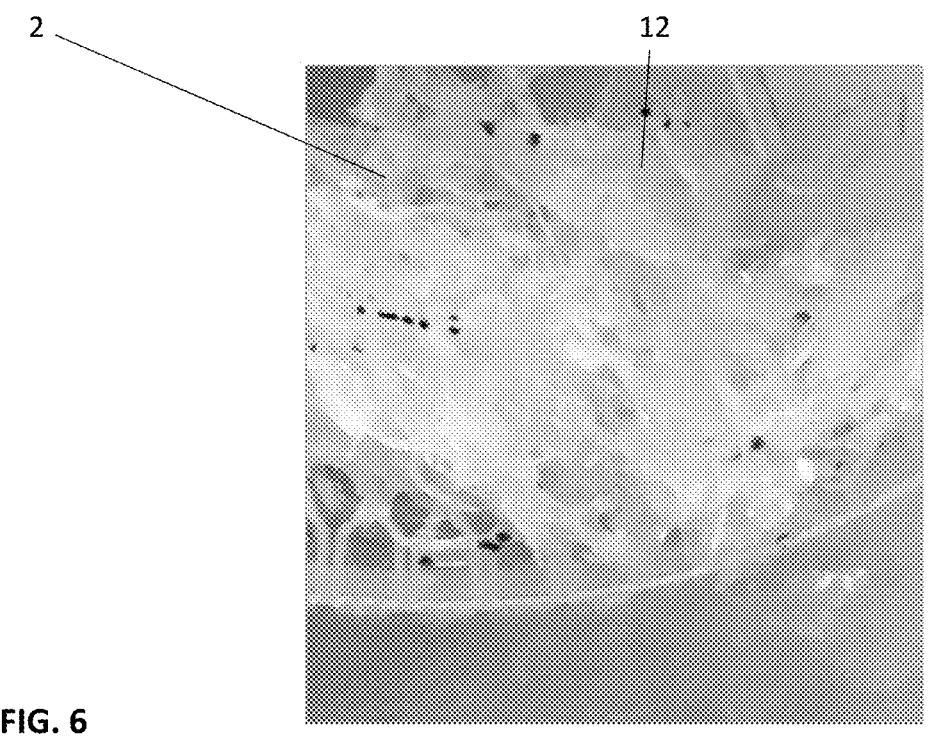
FIG. 6 is a photograph of exemplary cartilage fibers prior to washing.
Figure 7:
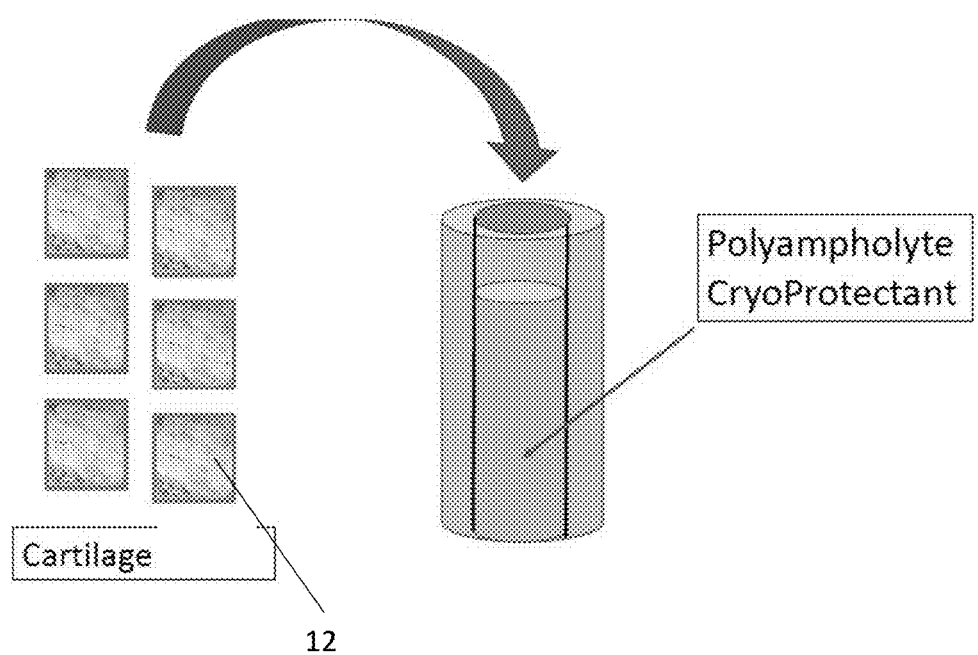
FIG. 7 depicts an alternative of infusing the particles with only the cryoprotectant.
Figure 8:
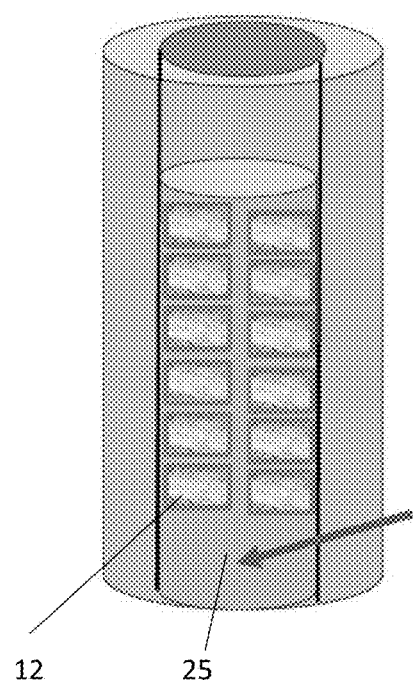
FIG. 8 further depicts the alternative of infusing the particles with only the cryoprotectant from FIG. 7.
Figure 9:
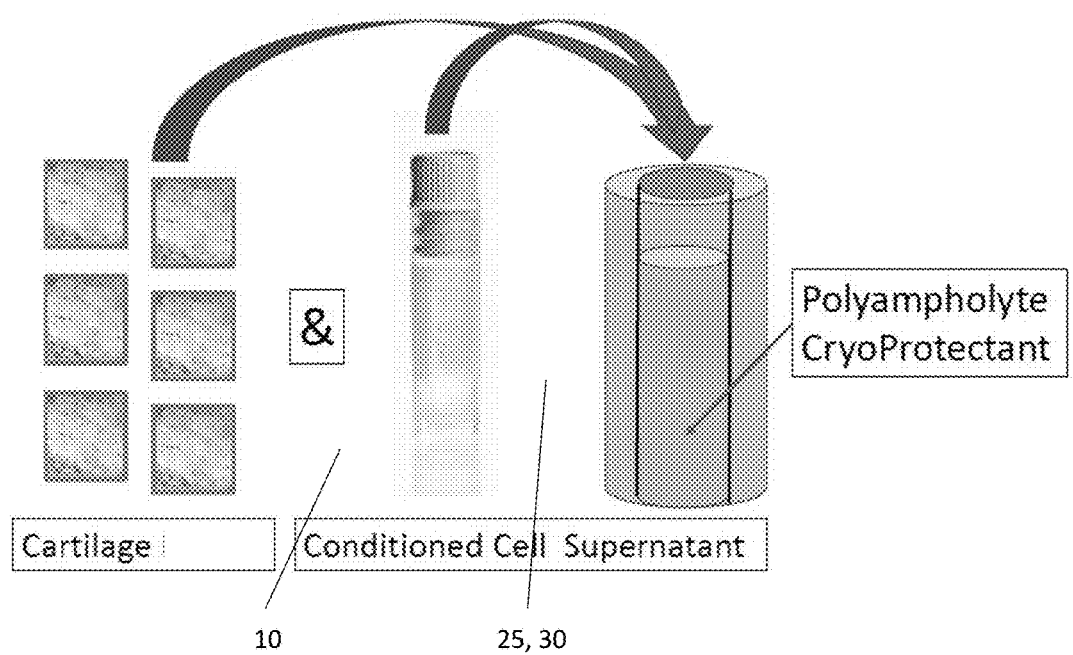
FIG. 9 depicts the cartilage particles and the conditioned cell supernatant to be infused in the polyampholyte cryoprotectant.
Figure 10:
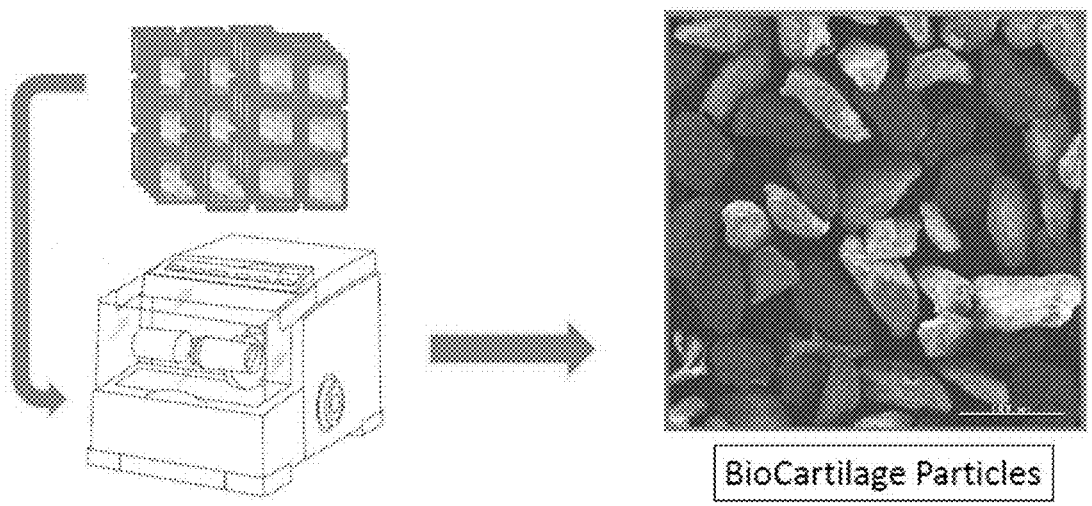
FIG. 10 is a schematic view of the cartilage fibers to be processed in a cryomill to result in biocartilage particles.
Figure 11:
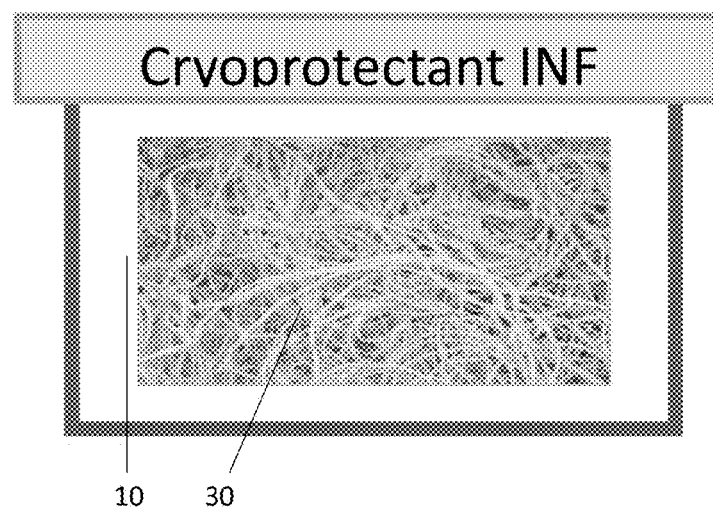
FIG. 11 illustrates the step of infusing the particles in the cryoprotectant.

With reference to FIG. 4, the cartilage tissue 2 in a schematic view is shown. In FIG. 5 and end view of the cartilage 2 is shown wherein cartilage shavings can be cut such that small segments parallel to the radial axis of the cartilage can be formed. These long segments can range in length from a few mm to a cm in length. The particles 12 shown in FIG. 6 prior to washing, when formed will be saline washed. Then the particles 12 after being saline washed can then be infused either under pressure or under vacuum with cryoprotectant, or with conditioned cells, or subcellular secretions from sorted, selected, or expanded cell lineages. As shown in FIG. 9, a supernatant 25 infusion is provided to the particles 12. As shown in FIG. 6, the supernatant 25 along with the particles 12 can further be infused with a cryoprotectant 30. Alternatively, the particles 12 can be infused with only the cryoprotectant 30, as shown in FIGS. 7 and 8 and also FIG. 11.

Figure 12:
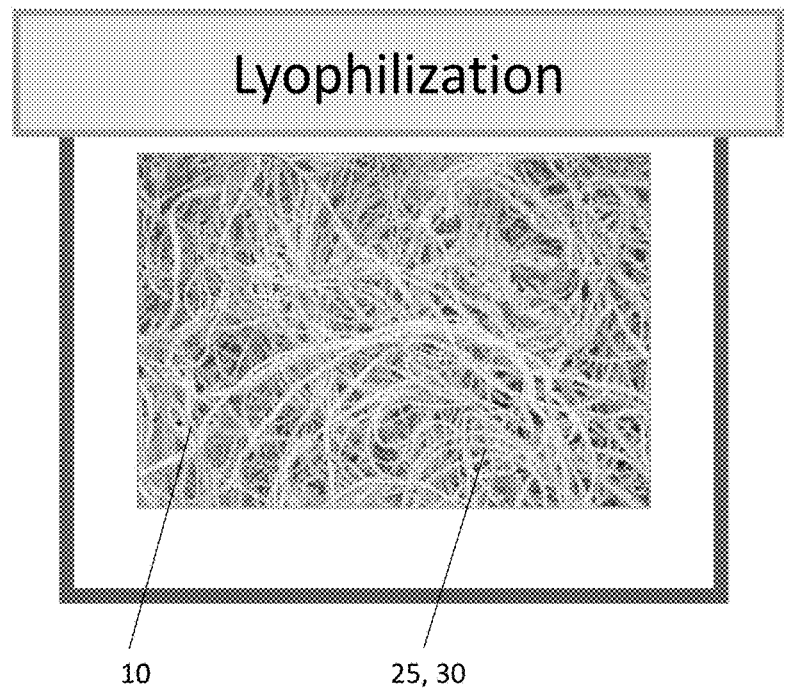
FIG. 12 illustrates the step of lyophilization of the cartilage particles.

After the cartilage particles 12 are infused with the supernatant 25 or cryoprotectant 30 or the combination of the supernatant 25 and the cryoprotectant 30, the infused cartilage particles 10 can then be lyophilized, as illustrated in FIG. 12.

Figure 13:
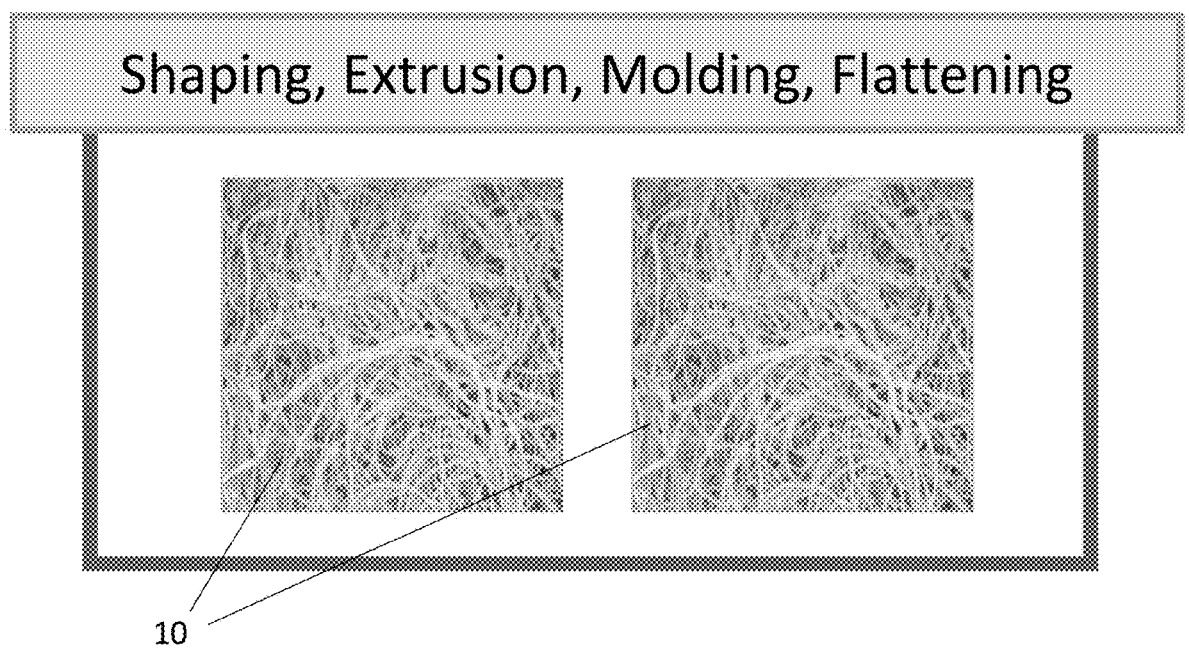
FIG. 13 illustrates forming the particles into a sheet or mat using the steps of shaping, extrusion, molding or flattening.
Figure 14:
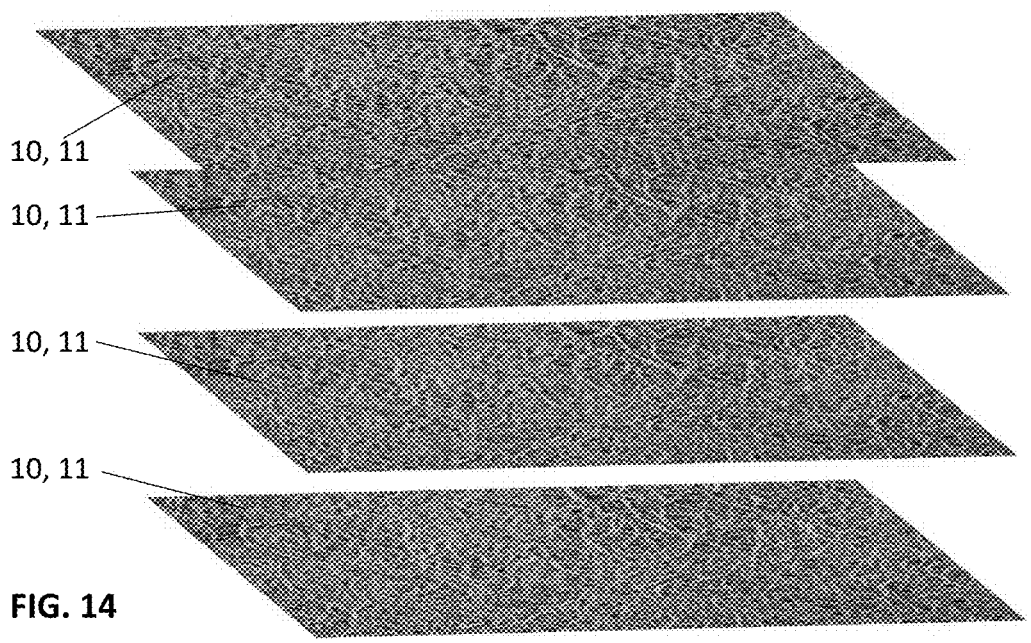
FIG. 14 schematically shows a plurality of the sheets or mats being stacked.

As shown in FIG. 13, the infused particles 10 shown as fibers can then be shaped, by extrusion, molding or flattening. The preferred shape is mats as illustrated in FIG. 14. The mats or sheets 11 can then be combined to form a laminate 15.

Figure 15:
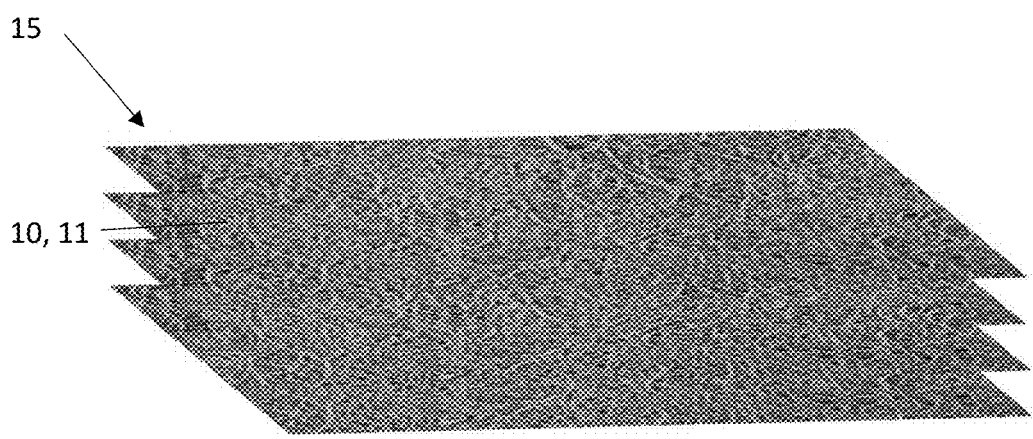
FIG. 15 schematically shows the stack being press fit.
Figure 16:
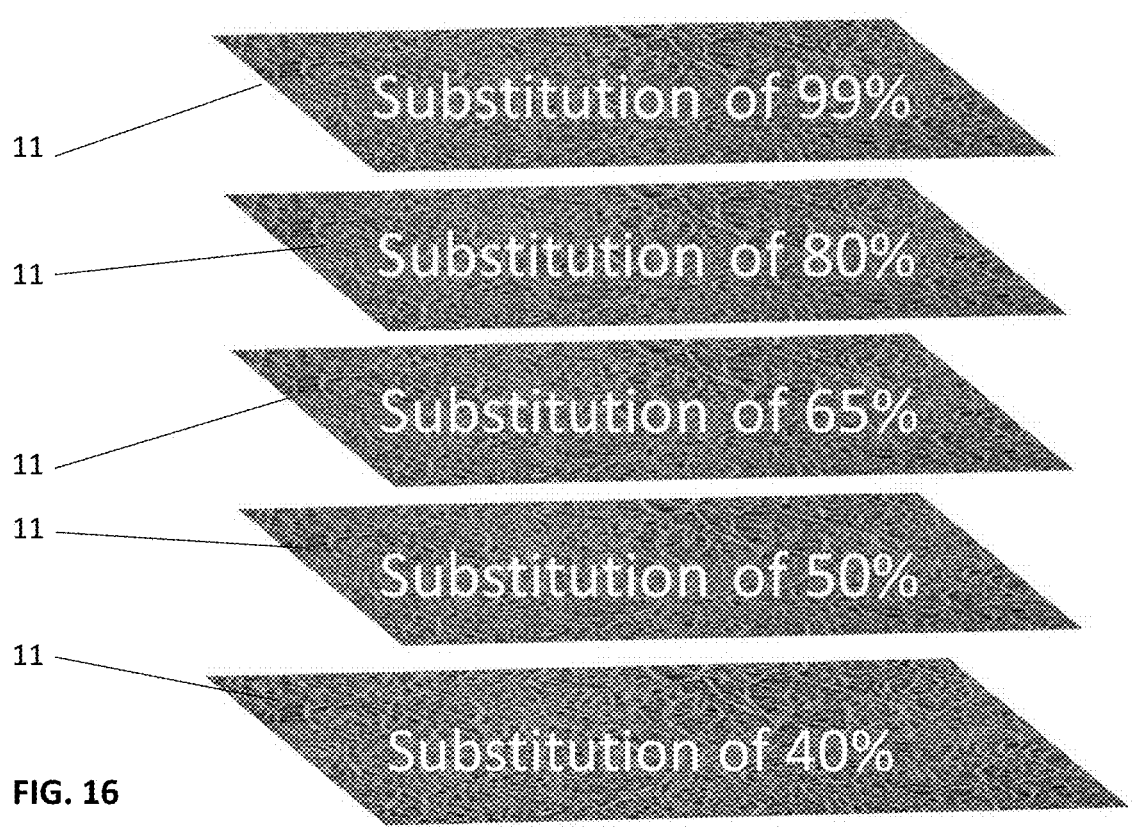
FIGS. 16 and 17 are diagrammatic views of sheets or mats with variation of C/A ratios.
Figure 17:
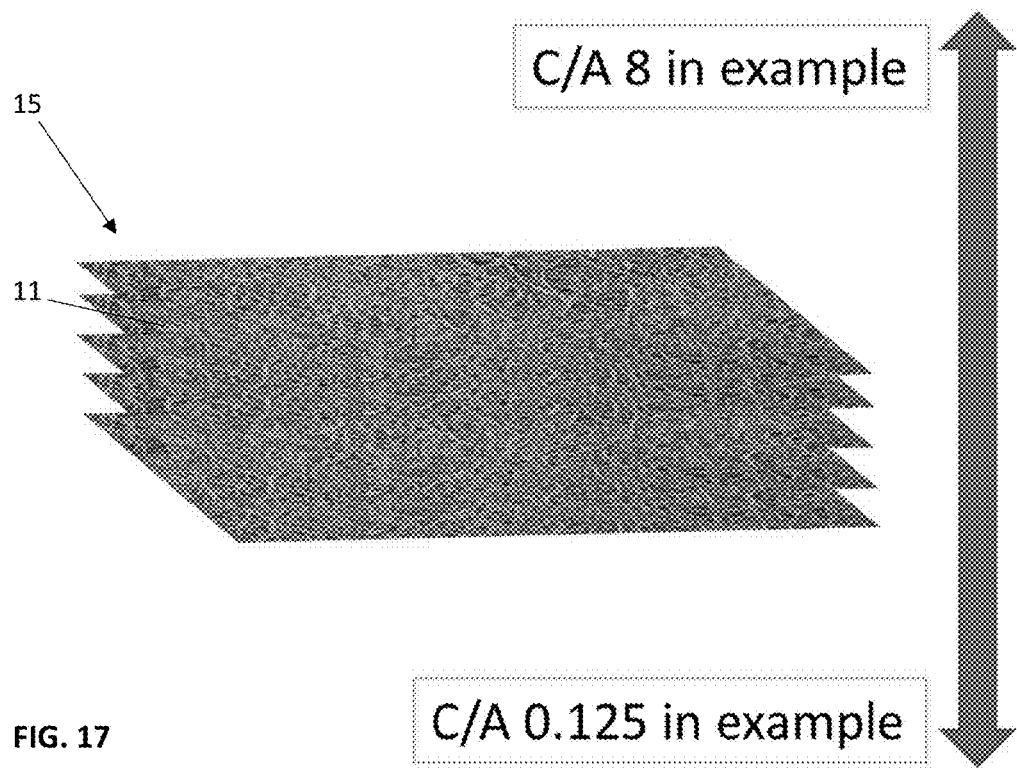
Figure 18:
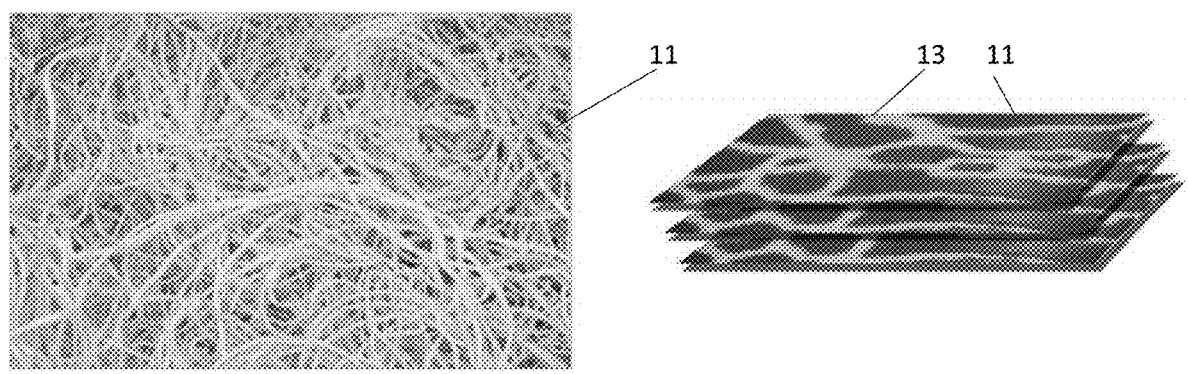
FIG. 18 is a view of a multilaminar sheet production.

As shown in FIG. 15, the laminate 15 is comprised of a plurality of sheets 11 of the infused cartilage particles 10 shown as fibers. These sheets 11, when compressed together to form the laminate 15, can be made in a unique way as illustrated in FIG. 16. FIG. 16 represents an embodiment of the invention wherein the cryoprotectant has been adjusted in terms of its carboxylic percentage. As shown, a substitution of 40, 50, 65, 80 and 99 percent carboxylic is illustrated in FIG. 16 When this material is combined to make the laminate 15, a variation in C/A ratio can occur as illustrated in FIG. 17. This ratio can vary in C/A from 0.125 as an example up to 8 as an example creating a wide variation in C/A ratio range available when employing this laminate. FIG. 18 shows the laminate made wherein each sheet has a pattern that has been formed on an upper surface of the sheet material 11. This pattern 13 can be a pattern of voids or mimetic pattern simulating cartilage if so desired.

Figure 19:
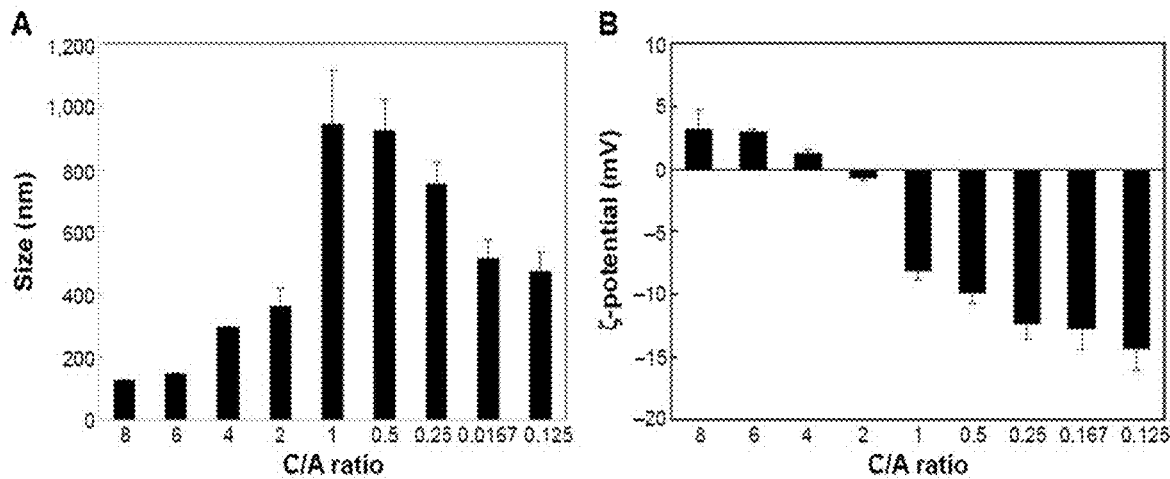
FIG. 19 is a pair of charts taken from the International Journal of Nanomedicine showing polyampholyte variation.

An important aspect of the C/A ratio variation is the different particle sizes shown in FIG. 19 that can be achieved by varying the C/A ratio. Additionally, the zeta potential B is illustrated in potential mV by a variation of the C/A ratio. By combining these two aspects, it is possible to create variations in charge and size of the particles created such as exosomes.

Figure 20:
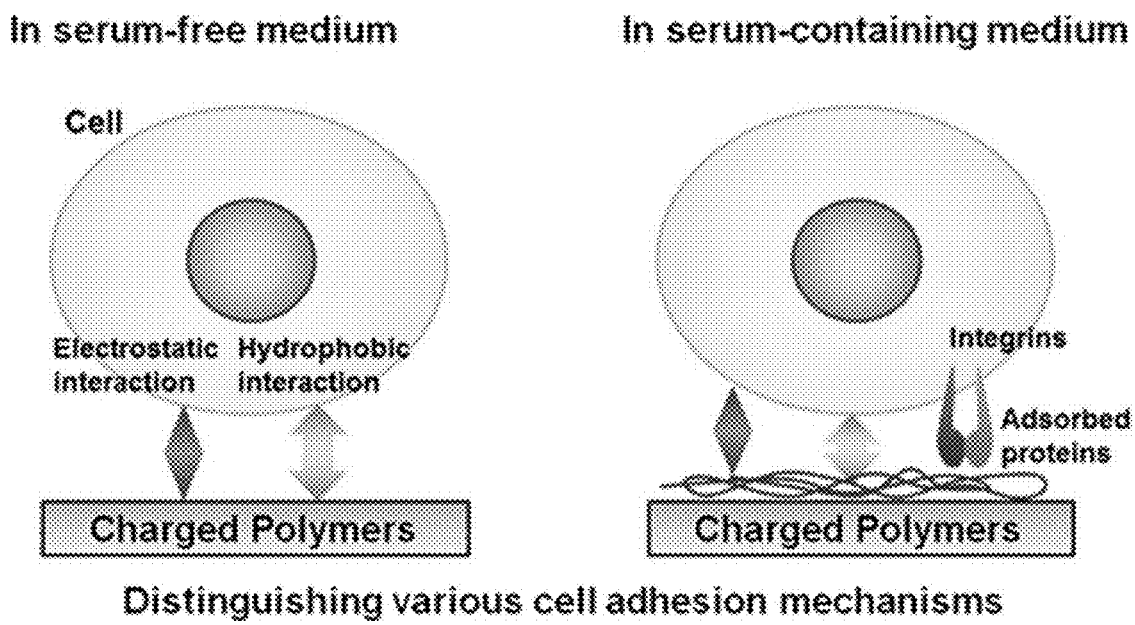
FIG. 20 is a chart showing the effects of charged polymers and cell adhesion.

FIG. 20 is an example of a serum free medium, wherein a cell is exposed to charged polymers and an electrostatic interaction and hydrophobic interaction occurs distinguishing the various cell adhesion mechanisms. Similarly, charged polymers can be provided if the polymers are charged positively and the cells have a negative charge, an absorption of proteins can be accelerated and enhanced in the serum containing medium as shown in FIG. 20.

For completeness of the understanding of the invention as described above, an example of one method of recovering the biological material from bone marrow is disclosed. It is understood that other sources and methods can be used to collect biologic material such as from bone, blood, fat cells, including the isolating of whole cells from these alternative sources from living hosts or cadavers and these cells would equally benefit from the present invention.

With reference to the exemplary method which is a tissue regenerative biological composition made from bone marrow 200, it is believed best understood by the methods used to process and recover the biological composition, as illustrated in the FIGS. 21-31.

Figure 21:
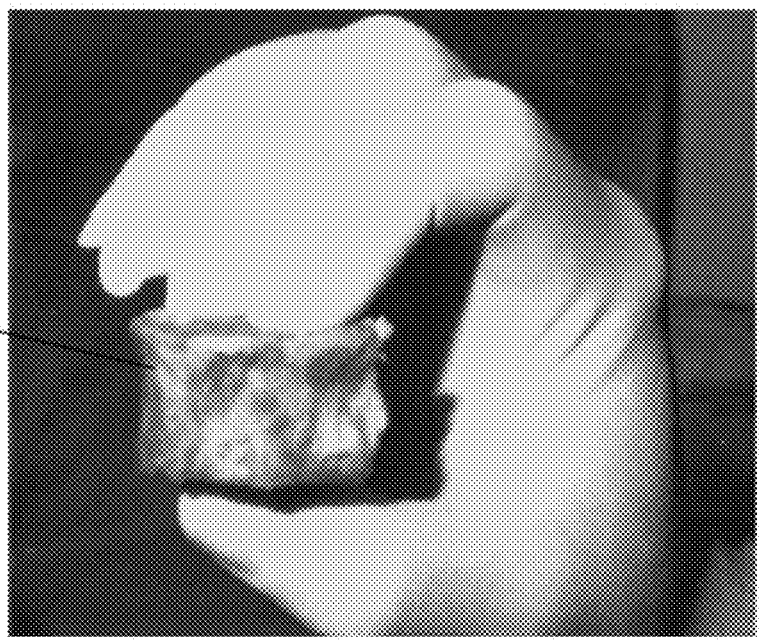
FIG. 21 shows a photograph of a cut vertebral body taken from a spine of a cadaver donor for use in a bone marrow derived biological composition.
Figure 22:
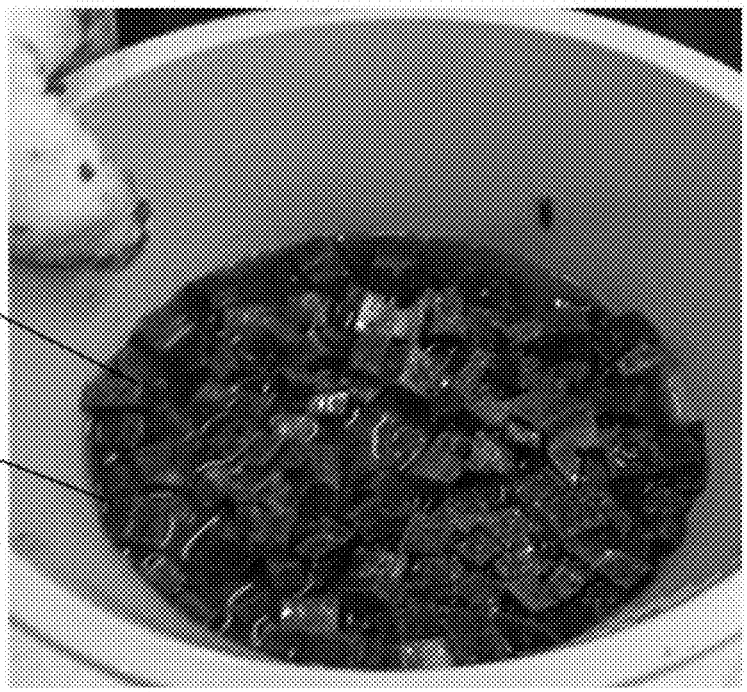
FIG. 22 shows a photograph of the vertebral body after being cut into cubic pieces and immersed in a packing media.
Figure 23:
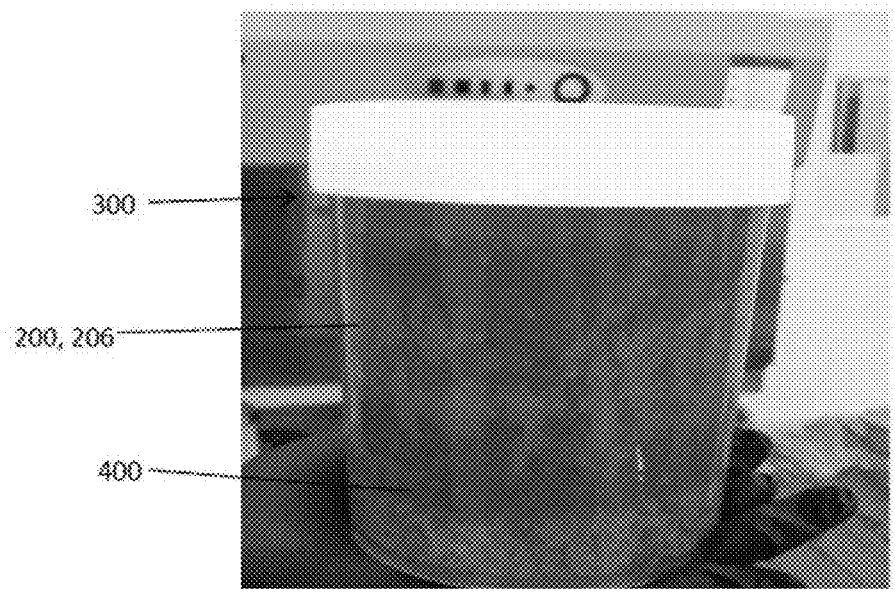
FIG. 23 shows a photograph of the bulk bone material after being ground and immersed in packing media and placed in a jar for later tumbling.
Figure 24:
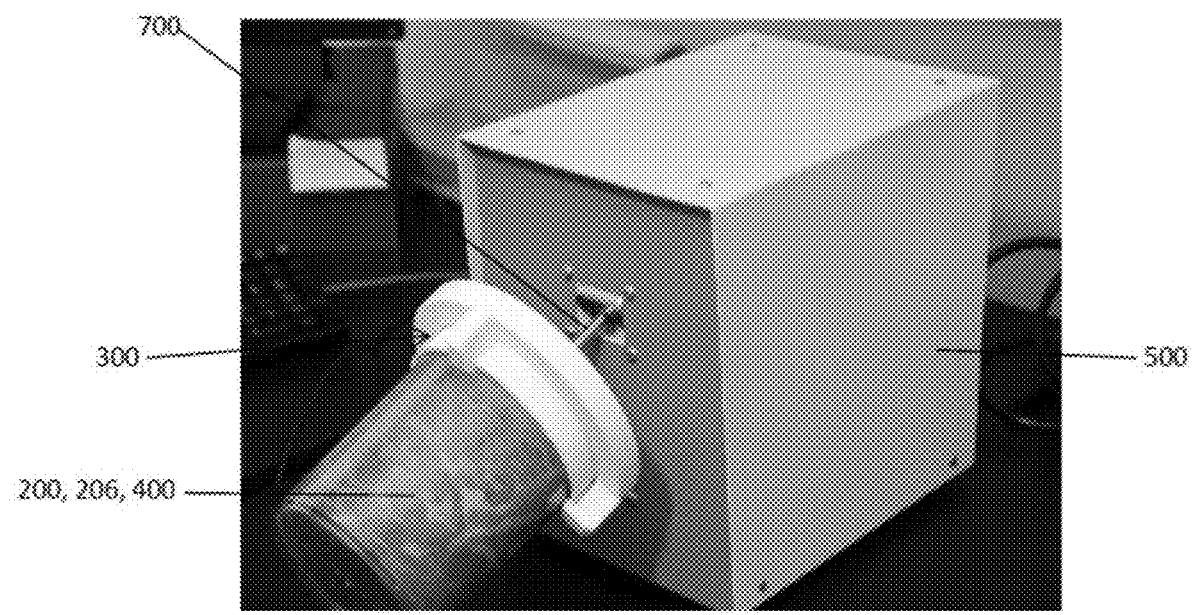
FIG. 24 shows a photograph of the jar with a CBT-Mixer connected to a tumbler.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (1 g/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 21.

Once a cleaned vertebral body 202 is obtained, the next step involves cutting each vertebral body 202 into pieces, each piece 204 roughly 1 cm$^3$. The cut pieces 204 being immersed in a packing media 400. The exemplary packing media can be DMEM with 0.5 ml Heparin and 1.25 ml of DNAse added.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400. At this point, the crushed bone 206, including cellular soft marrow 200, is intermixed.

Figure 25:
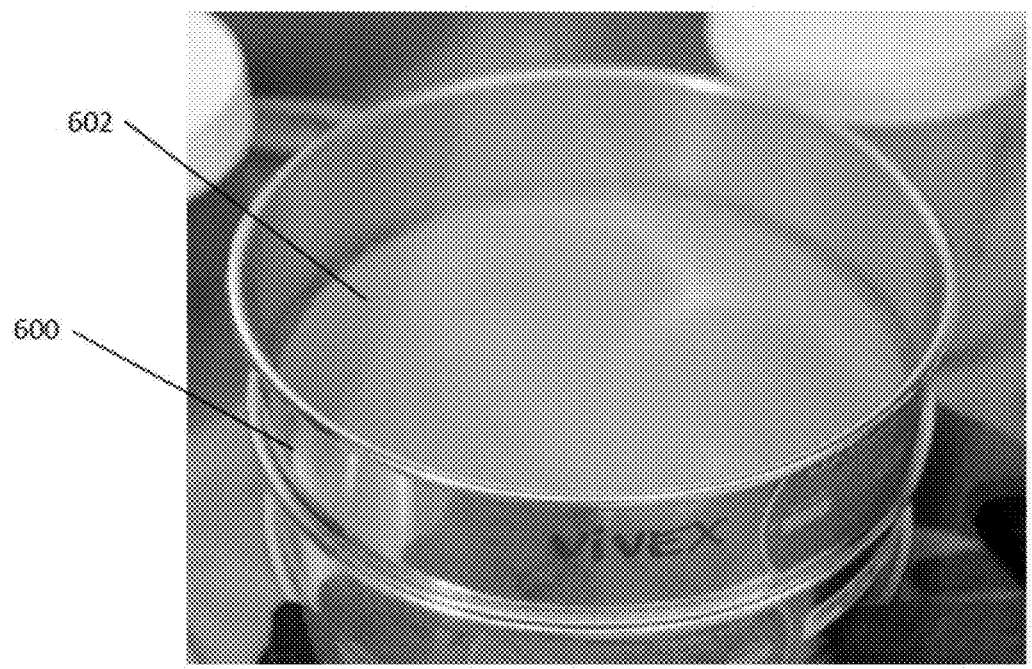
FIG. 25 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar with a CBT-Mixer in the jar. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 μm and 180 μm, as shown in FIG. 25.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-μm and the bottom pan sieve. Discard decanted fluid. | Use the 500-μm, 180-μm and bottom pan sieve. Collect decanted fluid. | Use the 500-μm, 180-μm and bottom pan sieve. Collect decanted fluid. | Use the 500-μm, 180-μm and bottom pan sieve. Collect decanted fluid. |
| Centrifuge | N/A | Use decanted fluid. | Use decanted fluid. | Use decanted fluid. |

Figure 27:
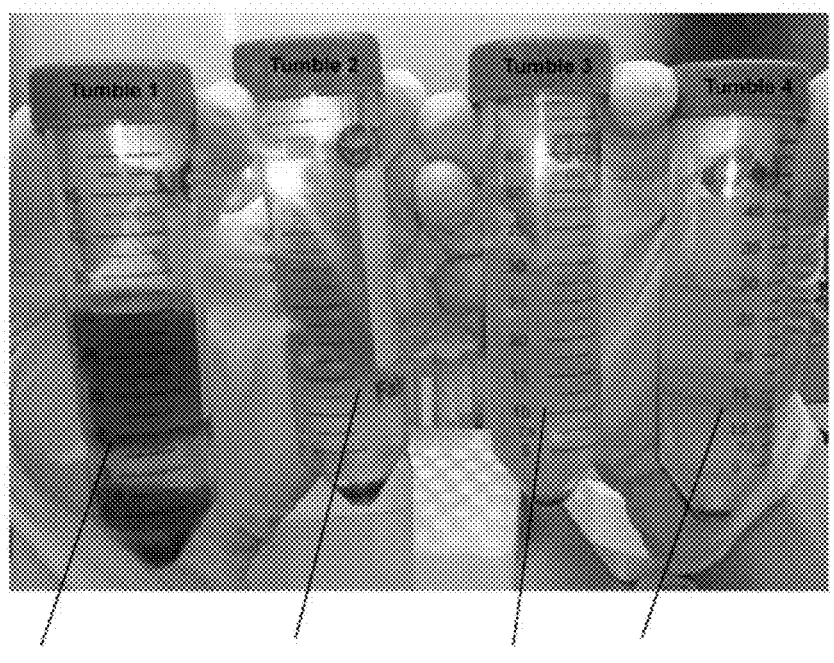
FIG. 27 is a photograph showing the four tumbling steps 1-4 by exemplary collection and Ficoll separation of the decanted fluids, the fluid in tumble 1 being completely discarded to remove unwanted debris.

In cycle 1, the decanted fluid 210 is discarded. To best understand this, an exemplary FIG. 27 shows conical tubes with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This FIG. 27 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid 220. Then the centrifugation of the combined decanted fluid 220 occurs by placing the fluid 220 in a number of 250 ml conical tubes using a 100 ml pipette. The centrifuge is programmed to 280×g for 10 minutes at room temperature, preferably about 20 degrees C. The fluid 220 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 26:
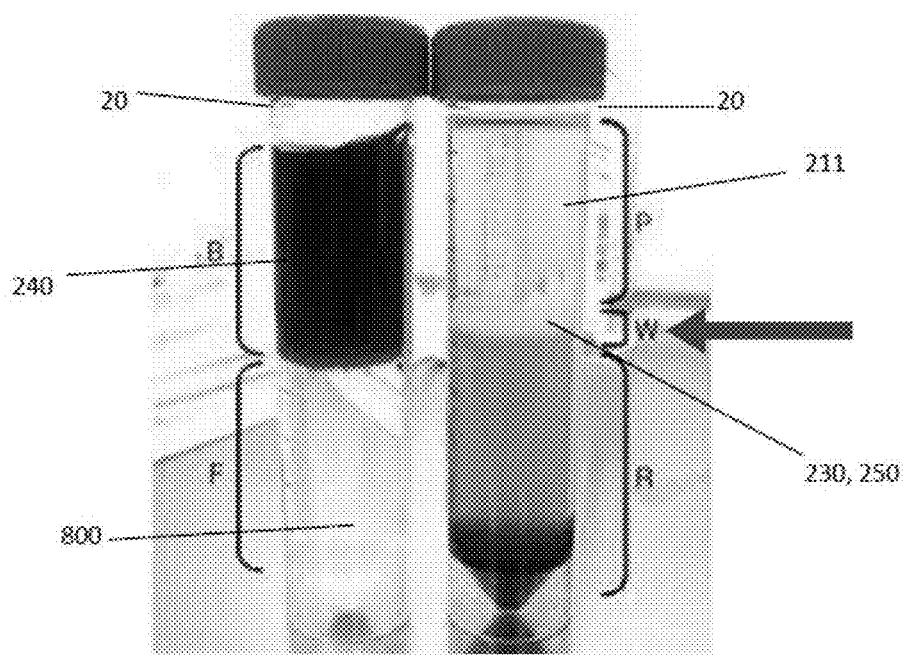
FIG. 26 shows a photograph of two 50-ml vials, the one on the left being prior to centrifuging with the Ficoll that is commercially available at the bottom and the material above it. The 50-ml vial on the right is after centrifuging showing the non-whole cell fraction interface layer.
Figure 28:
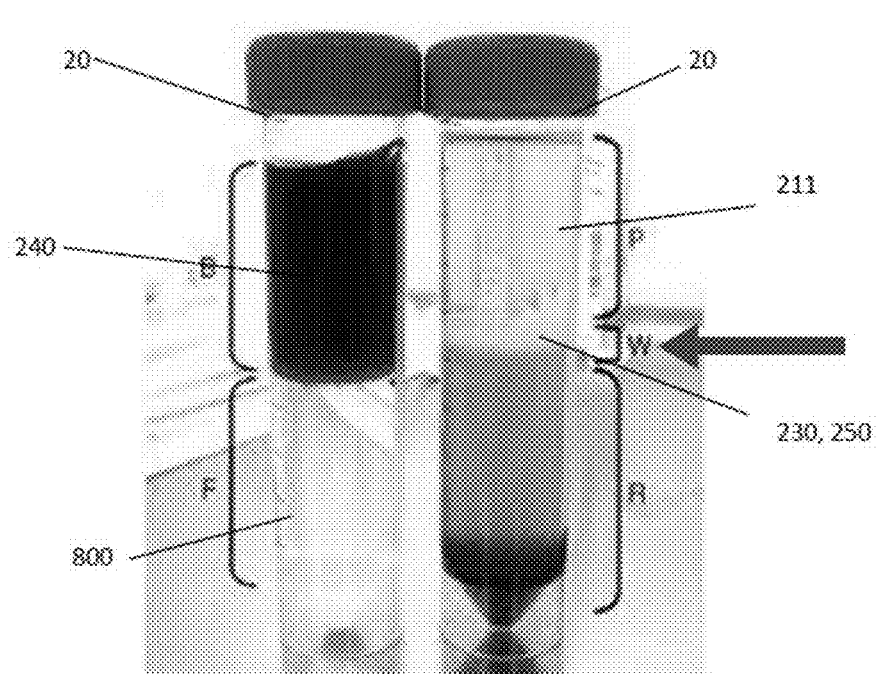
FIG. 28 shows a photograph of two 50 ml vials, the one on the left being prior to centrifuging with a sucrose gradient that is commercially available at the bottom and the material above it. The 50-ml vial on the right is after centrifuging showing the non-whole cell fraction above the interface layer.
Figure 29:
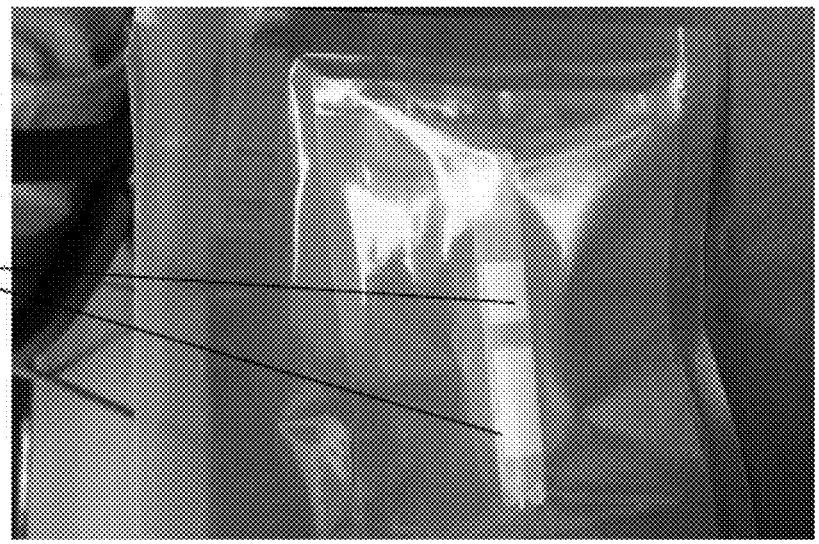
FIG. 29 is a representative photograph of the final packaging.

After this, as shown in FIGS. 26 and 28, the step of separating the cells 240 from the non-whole cellular components can occur by a density centrifugation, if so desired. The whole cells 240 are in the interface, often called the buffy layer, and the non-whole cell components are in the supernatant above the interface. The mixture is placed in 50 ml conical tubes 20 with Ficoll 800 and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid 211 above the interface 230 can be removed which includes the desired non-whole cell components and which excludes the whole cells 240, 250 or all the fluid 211 and the interface 230 can be removed together.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 μm filters. Exosomes are further collected and separated within the suspension in multiple centrifugation steps with increasing centrifugal strength to sequentially pellet cells (300 g), microvesicles (10,000 g) and ultimately exosomes (100,000 g). Cells can be deliberately removed to achieve a mixture having the non-whole cell fragments and microvesicles or can be kept forming a combination of whole cells and non-cellular components. An important aspect of the invention is the use of the supernatant with the buffy layer or interface with whole cells and be used together. In practice, the survival of the whole cells is not particularly relevant as the contents of the whole cells can be captured when the membrane of the whole cell is ruptured during processing. The cellular contents are bioactive, some as the acellular biologic material in the supernatant above the interface. All of these constituent elements can be used to form the biological mixture if so desired.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions that have been commercialized reduce the need for expensive equipment or technical know-how. Although their mode-of-action has not been disclosed or validated, these kits are commonly used.

Once the mixture is completed, the method can include additional steps.

When the mixture is prepared, it can have whole cells exclusively, or in combination, or even no whole cells, but will have the mechanically selected non-whole cellular components including vesicular components and active and inactive components of biological activity, cell fragments, cellular excretions, cellular derivatives, and extracellular components.

In one embodiment, the infused particle composition includes the sheets or mats into which the whole cells can be added. In that embodiment, it is possible to also provide particles with the whole cell either in a mixture or separately to be combined at the time of use.

Figure 30:
FIG. 30 is a photograph showing the cartilage particles.

In one embodiment, the cartilage is ground to a particle size of 100-300 μm, see FIG. 30. The cartilage mixture has 2.0 cc of cartilage particles 12, 3.0 cc of cartilage fibers 12F, yielding 40 percent and 60 percent respectively of the total 5 cc (5 gram) of cartilage. The ranges coincide with the 1 cc of biologic mixture when resuspended in 3 cc of saline to provide a mixture for implantation, which can be by packing, injection, scaffolding or any other suitable means, into a patient in a micro-fracture or tissue tear healing procedure, by way of example.

These particles as well can be infused according to the present invention.

Other ranges of particle sizes and mixtures can be employed depending on the application which, in this example, was cartilage regeneration. Lower volumes and concentrations may be more suited for less intrusive cartilage repairs or more if larger amounts of material are needed.

A cryopreservation liquid according to the invention is obtained by dissolving a polymer such as poly-lysine in physiological solutions by 1-50 w/w %; preferably by 2-20 w/w %, particularly preferably by 3-15 w/w %, and more preferably by 5-10 w/w %. The physiological solutions to be used are a physiological saline as well as culture media for culturing various cells and tissues. For example, Dulbecco-modified eagle MEM culture medium (DMEM) may be one of the preferable culture media. In place of, or in addition to poly-lysine, polyallylamines may be used. In place of these, or in addition to at least one of these, a compound(s) to be used is/are selected from other polyamines such as amino-group-introduced polysaccharides, and poly-amino acids such as poly-arginine, poly-glutamic acid and poly-aspartic acid; also a polysaccharide compound(s) that is/are selected from dextran, dextrin, pullulan and chitosan as well as polycarboxylic acid such as polyacrylic acid.

Among these polymers, preferable are polymers having a structure obtainable by polymerization of a monomer compound(s) that have both cationic and anionic substituent groups within the same monomer molecules; and especially preferable is poly-amino acids. In other words, especially preferable is a polymer having a repeating unit that has both amino and carboxyl groups. Poly-lysine to be used can be either ε-poly-L-lysine or ε-poly-D-lysine or α-poly-L-lysine. Cryoprotectant polymers have molecular weights between 100 and 100,000. The most preferable polymers fall into a group of ε-poly-L-lysine routinely used as food additives. These are either synthesized by enzymes or produced by the *Streptomyces* fungi and have the average molecular weights of 1000-20,000, and particularly those of 1000-10,000 with polymerization degrees ranging between 15-35, and those with 20 or lower are attempted to be produced. The average molecular weights or the average polymerization degrees are easily measurable by sodium dodecyl sulfate-polyacrylamide gel electrophoresis (SDS-PAGE), by using an electrophoresis apparatus as a means of evaluating density. Standard protein markers are used for the measurement. The poly-lysine may be heat-treated to increase its molecular weights greater than 30,000 and used as the polymer compound. However, the molecular weight range mentioned above is preferable due to the increasing viscosity with molecular weight. Because the poly-lysine having a free terminal carboxyl group has side-chain primary amino groups, their partial amidation by dicarboxylic anhydrides greatly gives excellent miscibility and solubilization performance described later. Other particularly favorable polymer compounds also adoptable according to the invention are polyallylamines with average molecular weights of 1000-1,000,000, preferably 1000-20,000. For examples, such adoptable polymers are: aqueous solution of the allylamine polymer (PAA-03 of Nitto Bosch Co., Ltd.) added with acetic anhydride or acetic acid; and the partially-methoxy-carbonylated allylamine polymer (PAA-U5000 of Nitto Bosch Co., Ltd.). The allylamine polymer, in same manner with the poly-lysine, has as side-chain groups primary amino groups only, but density of the primary amino group per unit molecular weight is larger in the allylamine polymer than in the poly-lysine. And, when the allylamine is partially carboxylated, obtained polymer compound is considered to act in same manner with partially-carboxylated poly-lysine mentioned later.

Preferably, the amino groups of the polyamine are partially blocked by being carboxylated or acetylated with carboxylic acid anhydride(s). This blockage is done by the carboxylation or acetylation of the amino groups to the degrees of preferably 50-99 mol %, particularly 50-93 mol %, more preferably 50-90 mol %, still more preferably 55-80 mol %, and the most preferably 58-76 mol %. About 50% of the amino group would be blocked by being reacted with 52-53 mol % of anhydrous carboxylic acid on basis of molar amount of the amino groups in the polyamine. In a normal reaction condition, 90-95% of the amino groups would be blocked when reacted with 100 mol % anhydrous carboxylic acid. The blocking rates above or below the above-mentioned ranges would decrease cryopreservation effects. Carboxylic acid anhydrides adoptable herein include acetic anhydride, citric anhydride, succinic anhydride, glutaric anhydride, malic anhydride, fumaric anhydride and maleic anhydride. Among these, succinic anhydride and acetic anhydride are particularly preferred.

However, polyamine with amino groups not blocked as free may also be used; thus adoptable are the degrees of carboxylation and acetylation throughout a range of 0-100 mol/mol %. In the present invention, polycarboxylic acid in which a part of the carboxyl groups is aminated may be used. More specifically, polycarboxylic acid may be partially aminated by reacting its carboxyl group with compounds such as diamine, triamine and the polyamine Adoptable diamines are ethylenediamine and hydrazides such as adipodihydrazide. Reaction of these amino compounds with carboxylic acid is by way of addition reaction with carbodiimide. In such occasion, adoptable is the degree of amination in a range of 0-100 mol/mol %. In same manner with blockage of amino groups, percentage of remaining carboxyl groups is preferably in a range of 50-99 mol %, more preferably in a range of 60-97 mol %, in each of which remaining percentage is for aminated carboxylic groups. For example, polyacrylic acid having average molecular weights of 1000-3,000,000, or 1000-10,000 in particular, is used; and 1-50 mol % of, preferably 3-40 mol % of, carboxyl groups of the polyacrylic acid are blocked with amines and carbodiimides such as ethylenediamine dihydrazide, or the like. Cryopreservation liquid according to the invention may also contain 0.3-15 w/w %, or 0.1-50 w/w % in particular, of conventional cryoprotectant materials such as DMSO, glycerol, ethylene glycol, trehalose or sucrose. Because cells are subject to damages caused by the oxidation stress during freezing and thawing, the addition of anti-oxidants to the cryoprotectant is expected to improve its preserving effects. For examples, anti-oxidants such as catalase, peroxidase, superoxide dismutase, vitamin E, vitamin C, polyphenols such as epigallocatechin gallate or glutathione may be used.

The osmotic pressure of the cryopreservation agent according to the invention is 200-1000 mOsm/kg, more preferably is 300-700 mOsm/kg, and further preferably 400-600 mOsm/kg. The cryopreservation agent according to the invention is applicable to the preservation of not only cells but also tissues. Examples of such cells and tissues to be cryopreserved by the cryopreservation agent are cultured cell lines, fertilized eggs of animal and human origin. Further examples are sperm cells, embryonic stem cells, IFS cells, mesenchymal stem cells, haemopoietic stem cells, neuronal stem cells, umbilical cord blood stem cells, hepatocytes, nerve cells, cardiomyocytes, vascular endothelial cells, vascular smooth muscle cells and blood cells. Not only animal or human cells but also plant cells can be included. Tissues and organs that are able to be preserved by the cryopreservation agent according to this invention are skins, nerves, blood vessels, cartilages, cornea, livers, kidneys, hearts and pancreatic islets.

Additional novelty of this invention is afforded in the variation in osmolality invigorated during the sublimation process. The loss of water suspends the materials in a static and transient state of relative harmony. With rehydration in the use of the product in saline, or in-patient care, or in common practice of combination with other allografts, differences extant to the original formulation are extended to new metabolic demands Variations in shape and thickness and absorption will define the destiny of whole, fragment, coated, fractured, and cellular organelles.

An interesting aspect of the present invention is the ability to adjust the pH from the preferred range of 7.4 to greater or lesser amounts. This allows the electro field charge to be adjusted greater or lower as a tailored means of increasing or decreasing the predetermined time for the coating to be metabolized. Alternatively, the mixture and the protectant can be diluted prior to implantation with sterile water or saline or host blood to thin the protectant coating to shorten the time to be metabolized if so desired. In any event, the present invention assures no rinsing or separation of the protectant from the cells is required insuring much higher survivability of the donor mixture.

Current understanding advanced in this continuation is adapted to note that once frozen, the material can be thawed, sublimated through a process of cryo-lyophilization, and that various concentrations of bone marrow collections of whole cells, cell fragments, exosomes, secretome packages, and free cytokines can be produced and admixed with allograft materials.

Such collected materials are stable at temperatures above freezing, and can be further combined with synthetic and organic polymers, embedded in particles, electrospun in fleece, adsorbed and absorbed by allografts, and used within the scope of biologic protection with minimal manipulation.

These processes can also be used to prepare a dense, bioactive derivative that can be mixed as a contribution to hydrogel cartridge technologies. Given the categorization of the polyampholyte as a hydrogel, the combination offers room temperature considerations to additive manufacturing technologies using bio inks. Printability of a biomaterial is determined by the printing technique. Although a wide range of biomaterial inks including polymers, ceramics, hydrogels and composites have been developed, the field struggles with processing these materials into self-supporting devices with tunable mechanics, degradation, and bioactivity. The development of an allograft laden hydrogel affords such potentials.

The current invention defines a cartilage grafting material principally defined by particle morphology derived from cartilage and subsequently infused with non-whole cell supernatant derived from fatty and cellular marrow, stromal vascular fraction, interstitial fluid, and free water content supporting skeletal tissue. The collagen, and non-collagenous proteins, lipids, and amino acids infused into the grafting material may be further protected by infiltrating a polyampholyte cryoprotectant, or combinations of polyampholyte cryoprotectant with supernatant that are similarly infused prior to being formed, shaped, or cryo-lyophilized. Cartilage particles fabricated by this technology can be matted, molded, woven, braided, embossed with mimetic topography, stacked to create laminates, further combined with cells fully differentiated to osteocyte phenotype, or stem cells retaining multi-lineage potential to support restitution of deficits, or sustain regeneration of cartilage following traumatic damage. As shown in FIGS. 14-18, the infused matrices can be fabricated as stacked laminate varying in thickness and charge attendant to polyampholytes composition. The stacked lamina individually assemble or define a resultant charge potential in conjunction with the plied depth of the material and proportional to the specific polyampholyte charge concentrations used in each. In example, matted, rolled, flattened, or embossed materials, develop zeta potential by design and offers analog mimetic as a non-digital remedy to guide biochemical equilibrium when tissues are rewetted. Essentially, this invention defines a gradient of growth factors, non-whole cell constituents, polyampholyte charge, combinations with cells, and an electrically motile graft material. By intention the marrow constituency effecting equilibrium between stroma, cell, interstitial fluid is guided to direction and dimension of the invention.

In one embodiment, the composition of infused cartilage particles is made by a process wherein the cartilage particles are prepared as described above and the supernatant of biologic material is intermixed with the cartilage particles making a mixture of cartilage particles and supernatant; and that combination is suspended in the cryoprotectant of polyampholyte. The suspension of the material in the cryoprotectant can then be treated under pressure or vacuum to ensure the biologic material in the cryoprotectant is sufficiently infused into the cartilage particles. Thereafter, the composition can be frozen or cryopreserved or alternatively can be freeze-dried. The cartilage particles, prior to being intermixed with the supernatant, can be either fresh cartilage particles or cartilage particles that have been dried using hypothermic drying, air drying or even freeze-drying. The advantage of drying the cartilage material versus using fresh cartilage material is that the material is more hydrophilic and will tend to draw the supernatant into the cartilage particles along with the polyampholyte cryoprotectant. An important advantage of the material being coated with the polyampholyte cryoprotectant is that the cartilage material is more bioactive and retains sufficient activity that it can induce new generation of cartilage for repair of microfractures or tears in a patient's cartilage. The infused particle composition, once prepared, is suitable for direct implantation into the patient. In the case of the freeze-dried infused particles, the infused particles can be diluted in the patient's own blood, or alternatively saline solution prior to implanting so the infused particles can have a wet consistency prior to application. In the case of the frozen or cryopreserved infused particles composition, the composition is simply thawed and can be implanted directly into the patient for repair of any cartilage defect.

Components of the supernatant have shown, in the case of bone marrow derived material, that the exosomes within the supernatant have an increased osteoinductive capacity compared to exosome material that has been freeze-dried without the cryoprotectant. This is significant in that in order for the cartilage particles to be enhanced for use in cartilage defects, it is important that the material be sufficiently biologically compatible with the cartilage material to be repaired.

As a supplement to the infused cartilage particles, it is also possible to intermix the cartilage particles with cartilage fibers that have a length of 6000 microns or less. These ground fibers can then be intertwined in the particles along with the supernatant of biological material such that the elongated fibers in combination with the particles can constitute the cartilage component of the infused cartilage composition.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making infused non-demineralized cartilage particles comprises:
   cutting or shaving cartilage tissue into particles;
   washing the particles; and
   infusing the particles with a supernatant of biologic material or a polyampholyte cryoprotectant or a combination of both to create infused particles.

2. The method of claim 1 wherein the step of infusing includes exposing the particles to a negative pressure or vacuum to draw the supernatant and/or the polyampholyte cryoprotectant into the particles.

3. The method of claim 1 wherein the step of infusing includes exposing the particles to a positive pressure to drive the supernatant and/or the polyampholyte cryoprotectant into the particles.

4. The method of claim 1 wherein the particles are ground into an aspherical shape.

5. The method of claim 1 further comprises freezing the supernatant and/or the polyampholyte cryoprotectant infused particles.

6. The method of claim 1 wherein the step of cutting or shaving includes passing the cartilage tissue through a cutting die to form shaped particles.

7. The method of claim 6 wherein the shaped particles have a Non-symmetrical randomness that mirrors the structural intricacy of biological tissues as infinitesimally variable.

8. The method of claim 1 further comprises the step of drying the infused particles.

9. The method of claim 8 wherein the step of drying includes freeze-drying by lyophilization.

10. The method of claim 8 further comprises one or more of the steps of shaping, extrusion, molding or flattening the dried particles into sheets to form random particle stacked matting.

11. An infused composition comprises non-demineralized cartilage particles taken from cartilage and infused by pressure or vacuum at ambient temperature with a supernatant of biologic material and a polyampholyte cryoprotectant wherein the supernatant is derived from one or more of a cellular fat, cellular marrow or cellular placental tissues.

12. The infused composition of claim 11 wherein the supernatant includes a mixture of biologic material having non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function.

13. The infused composition of claim 12 wherein a volume of a polyampholyte cryoprotectant is intermixed with the supernatant including the mixture of biologic material.

14. The infused composition of claim 12 wherein the polyampholyte cryoprotectant forms a three-dimensional infusion impregnating and coating externally enveloping each of the cartilage particles along with each of the non-whole cellular components, if any, and each of the whole cells, if any, of the mixture of biologic material.

15. The infused composition of claim 12 wherein the infusion buffers inflammation.

16. The infused composition of claim 12 wherein the polyampholyte cryoprotectant is a liquid of a polyamine polymer compound of carboxylated poly-lysine.

17. The infused composition of claim 12 wherein the infusion sustains regenerative potential and biologic function of the mixture during preservation and implantation.

18. The infused composition of claim 12 wherein the infusion coating is configured to be metabolized after implantation after a predetermined time of three or more days up to six days.

19. The infused composition of claim 11 wherein the infused particles are randomly compressed into a matting or sheet.

20. The infused composition of claim 19 wherein a plurality of the matting or sheets are stacked to form a laminated stack.

21. The infused composition of claim 19 wherein each sheet or mat can have a distinct cation/anion ratio between nitrogen atoms of a cationic polymer and carboxyl groups of an anionic polymer and stacking the sheets or mats together is configured to create a range variation of cation/anion ratios across the layers of the laminate to control nano-dimensions accentuating zeta potential for enhancing exosome absorption by creating a gradient of molecular potential when implanted.

22. The infused composition of claim 12 wherein the polyampholyte cryoprotectant forms a strong hydrophilic characteristic of the infusion coating to protect the non-whole cellular components if any and the contents of the whole cells if any.

23. The infused composition of claim 12 wherein the mixture is mechanically selected biologic material derived from one of fat cells, placental cells, bone marrow, or other somatic cells maintaining organelle consistency and tissue typing.

24. The infused composition of claim 23 wherein the mixture of mechanically selected biologic material further includes a select number of non-whole cell fractions including one or more of exosomes, transcriptosomes, proteasomes, membrane rafts, lipid rafts.

25. The infused composition of claim 12 wherein the biological mixture is predisposed to demonstrate or support elaboration of active volume or spatial geometry consistent in morphology with that of articular cartilage.

26. The infused composition of claim 12 wherein the biological mixture extends regenerative resonance that complements or mimics tissue complexity.

27. The infused composition of claim 12 wherein the biological mixture is treated in the cryoprotectant prior to preservation or cryopreservation or freeze drying.

28. The infused composition of claim 12 wherein the cryoprotectant creates a physical or electrical or chemical gradient or combination thereof for tissue regeneration.

29. The infused composition of claim 28 wherein the physical gradient has a physical characteristic of modulus or topography such as charge density, field shape or cyto-taxic, cryo- or chemo- taxic tendencies.

30. The infused composition of claim 28 wherein the chemical gradient has a chemical characteristic of spatially changing compositions of density or species of functional molecules, wherein the molecules can offer a fixed catalytic function as a co-factor.

31. The infused composition of claim 28 wherein the electrical gradient has an electrical characteristic of charge based or pH based or electron affinities that confer metastability in biologic potential.

32. The infused composition of claim 23 wherein the mixture is mechanically selected biologic material derived from bone marrow wherein the bone marrow which is derived from a cadaver has separation-enhanced non-whole cell fractions vitality including one or more of the following: separating the fractions from cells heightens their vitality, reversing "arrest" of donors, accentuating responsive molecular coupling, matrix guarding in neutralizing inflammation or providing a basis for metabolic satience by balancing stimulus for repair.

33. The infused composition of claim 12 wherein the polyampholyte cryoprotectant is a polyampholyte of carboxylated polylysine and wherein the percentages of carboxylation is altered to control exosome size, matrix voltages and/or zeta potential.

34. The infused composition of claim 12 wherein a regenerative resonance occurs in the presence or absence of a refractory response.

35. The infused composition of claim 12 wherein a cryopreservation occurs at a temperature that is sub-freezing.

36. The infused composition of claim 12 wherein a cryopreservation occurs at a temperature from 0 degrees C. to −200 degrees C.

37. The infused composition of claim 12 wherein the mixture creates a physical or electrical or chemical gradient or combination thereof for tissue regeneration.

38. The infused composition of claim 37 wherein the gradient has a physical characteristic such as modulus or topography.

39. The infused composition of claim 37 wherein the gradient has a chemical characteristic such as spatially changing compositions of density or species of functional molecules.

40. The infused composition of claim 37 wherein the gradient has an electrical characteristic such as charge based or pH based.

41. The infused composition of claim 11 wherein the biological mixture contains organelle fragments.

42. The infused composition of claim 40 wherein the electrical characteristic has a positive zeta potential formed in the infused composition to ensure uptake of nano-particles into cells when implanted as a result of a positive surface charge causing an electrostatic interaction between negatively charged cellular membranes and the positively charged infused particles.

43. The infused composition of claim 37 wherein the composition is maintained at ambient temperature prior to freeze drying.

44. The infused composition of claim 11 wherein the particles are infused with the polyampholyte cryoprotectant for direct implantation wherein said polyampholyte cryoprotectant is a 1-50 w/w % aqueous solution of at least one polyamine polymer compound comprised of at least one polymer of units having side-chain amino groups, said at least one polymer of units being selected from a group consisting of ε-poly-L-lysine, α-poly-L-lysine, poly-arginine, allylamine polymer and partially methoxy-carbonylated allylamine polymer; and 50-99 mol % of amino groups, other than those forming amino-acid-to-amino-acid linkages, of said at least one polymer compound is blocked with carboxylic anhydride to form pendant moieties, each of which is linked to main chain of the polymer via an amide linkage and essentially has a not-blocked carboxylic group.

45. The infused composition intermixed with the polyampholyte cryoprotectant of claim 44 wherein said polyampholyte cryoprotectant is obtained by dissolving the at least one polyamine polymer compound in a physiological solution.

46. The infused composition intermixed with the polyampholyte cryoprotectant of claim 45 wherein the physiological solution is a saline, Dulbecco-modified eagle MEM culture medium (DMEM), or a culture medium for cells or tissues.

47. The infused composition intermixed with a polyampholyte cryoprotectant of claim 44 wherein said at least one polymer compound is ε-poly-L-lysine having number-average molecular weight in a range of 1000-20,000.

48. The infused composition intermixed with a polyampholyte cryoprotectant of claim 44 wherein remaining side-chain amino groups or remaining side-chain and terminal amino groups of the at least one polymer compound are not blocked by covalent bonding.

\* \* \* \* \*